United States Patent
Spilker et al.

(10) Patent No.: US 10,390,885 B2
(45) Date of Patent: Aug. 27, 2019

(54) METHOD AND SYSTEM FOR DETERMINING TREATMENTS BY MODIFYING PATIENT-SPECIFIC GEOMETRICAL MODELS

(71) Applicant: HeartFlow, Inc., Redwood City, CA (US)

(72) Inventors: Ryan Spilker, Redwood City, CA (US); David Eberle, San Francisco, CA (US); Leo Grady, Millbrae, CA (US)

(73) Assignee: HeartFlow, Inc., Redwood City, CA (US)

( * ) Notice: Subject to any disclaimer, the term of this patent is extended or adjusted under 35 U.S.C. 154(b) by 322 days.

(21) Appl. No.: 15/265,284

(22) Filed: Sep. 14, 2016

(65) Prior Publication Data

US 2017/0007332 A1    Jan. 12, 2017

Related U.S. Application Data

(63) Continuation of application No. 15/080,955, filed on Mar. 25, 2016, which is a continuation of application
(Continued)

(51) Int. Cl.
*A61B 34/10*    (2016.01)
*G06F 17/50*    (2006.01)
(Continued)

(52) U.S. Cl.
CPC .......... *A61B 34/10* (2016.02); *G06F 17/5009* (2013.01); *G06F 19/321* (2013.01);
(Continued)

(58) Field of Classification Search
CPC .............. A61B 34/10; A61B 2034/104; A61B 2034/105; A61B 2034/107; G06T 7/11;
(Continued)

(56) References Cited

U.S. PATENT DOCUMENTS

| 6,236,878 B1 | 5/2001 | Taylor |
| 7,526,112 B2 * | 4/2009 | Murphy ............... G06T 7/0012 128/922 |

(Continued)

FOREIGN PATENT DOCUMENTS

| CN | 102346811 A | 2/2012 |
| WO | WO 2007/101346 A1 | 9/2007 |
| WO | WO 2012/021307 A2 | 2/2012 |

OTHER PUBLICATIONS

Office Action from corresponding EP Application No. 14712409.3, dated Nov. 16, 2015 (8 pages).
(Continued)

*Primary Examiner* — Manav Seth
(74) *Attorney, Agent, or Firm* — Bookoff McAndrews, PLLC

(57) ABSTRACT

Systems and methods are disclosed for evaluating cardiovascular treatment options for a patient. One method includes creating a three-dimensional model representing a portion of the patient's heart based on patient-specific data regarding a geometry of the patient's heart or vasculature; and for a plurality of treatment options for the patient's heart or vasculature, modifying at least one of the three-dimensional model and a reduced order model based on the three-dimensional model. The method also includes determining, for each of the plurality of treatment options, a value of a blood flow characteristic, by solving at least one of the modified three-dimensional model and the modified reduced order model; and identifying one of the plurality of treatment options that solves a function of at least one of: the determined blood flow characteristics of the patient's heart or vasculature, and one or more costs of each of the plurality of treatment options.

20 Claims, 23 Drawing Sheets

Related U.S. Application Data

No. 14/323,300, filed on Jul. 3, 2014, now Pat. No. 9,449,146, which is a continuation of application No. 13/782,307, filed on Mar. 1, 2013, now Pat. No. 9,042,613.

(51) Int. Cl.
| | |
|---|---|
| G06F 19/00 | (2018.01) |
| G06K 9/00 | (2006.01) |
| G06K 9/46 | (2006.01) |
| G06K 9/66 | (2006.01) |
| G06T 7/00 | (2017.01) |
| G06T 7/20 | (2017.01) |
| G06T 7/11 | (2017.01) |
| G16H 50/50 | (2018.01) |
| G16H 50/20 | (2018.01) |

(52) U.S. Cl.
CPC ..... *G06F 19/3481* (2013.01); *G06K 9/00335* (2013.01); *G06K 9/46* (2013.01); *G06K 9/66* (2013.01); *G06T 7/0012* (2013.01); *G06T 7/11* (2017.01); *G06T 7/20* (2013.01); *G16H 50/20* (2018.01); *G16H 50/50* (2018.01); *A61B 2034/104* (2016.02); *A61B 2034/105* (2016.02); *A61B 2034/107* (2016.02); *G06K 2009/4666* (2013.01); *G06T 2207/20112* (2013.01); *G06T 2207/30096* (2013.01); *G06T 2207/30101* (2013.01); *G06T 2207/30104* (2013.01)

(58) Field of Classification Search
CPC .......... G06T 7/0012; G06T 7/20; G06T 2207/20112; G06T 2207/30096; G06T 2207/30101; G06T 2207/30104; G16H 50/50; G16H 50/20; G06F 17/5009; G06F 19/00; G06F 19/321; G06F 19/3481; G06K 9/00335; G06K 9/46; G06K 9/66; G06K 2009/4666

See application file for complete search history.

(56) References Cited

U.S. PATENT DOCUMENTS

| | | | | |
|---|---|---|---|---|
| 7,860,283 | B2* | 12/2010 | Begelman | A61B 5/02007 345/418 |
| 7,873,194 | B2* | 1/2011 | Begelman | A61B 5/02007 345/418 |
| 7,940,970 | B2* | 5/2011 | Levanon | A61B 5/02007 378/4 |
| 7,940,977 | B2* | 5/2011 | Begelman | G06T 7/62 128/922 |
| 8,273,404 | B2* | 9/2012 | Dave | A61L 31/06 427/2.24 |
| 8,290,228 | B2* | 10/2012 | Cohen | A61B 5/0044 382/128 |
| 8,311,747 | B2* | 11/2012 | Taylor | A61B 5/02007 702/19 |
| 8,315,812 | B2* | 11/2012 | Taylor | A61B 5/02007 702/19 |
| 8,670,603 | B2* | 3/2014 | Tolkowsky | A61B 5/0044 382/130 |
| 8,781,193 | B2* | 7/2014 | Steinberg | A61B 5/0044 382/130 |
| 9,008,754 | B2* | 4/2015 | Steinberg | A61B 5/0044 600/424 |
| 9,042,613 | B2* | 5/2015 | Spilker | G16H 50/20 382/128 |
| 9,084,531 | B2* | 7/2015 | Chen | A61B 5/0033 |
| 9,189,600 | B2* | 11/2015 | Spilker | G16H 50/20 |
| 9,216,065 | B2* | 12/2015 | Cohen | A61B 5/0044 |
| 9,349,178 | B1* | 5/2016 | Itu | G16H 50/50 |
| 9,449,146 | B2* | 9/2016 | Spilker | G16H 50/20 |
| 9,538,925 | B2* | 1/2017 | Sharma | A61B 5/0261 |
| 10,052,158 | B2* | 8/2018 | Taylor | A61B 5/02007 |
| 2004/0049115 | A1 | 3/2004 | Murphy et al. | |
| 2005/0187461 | A1 | 8/2005 | Murphy et al. | |
| 2006/0008786 | A1* | 1/2006 | Feygin | G09B 23/285 434/262 |
| 2007/0014452 | A1 | 1/2007 | Suresh et al. | |
| 2008/0020362 | A1 | 1/2008 | Cotin et al. | |
| 2008/0219308 | A1 | 9/2008 | Yamanishi et al. | |
| 2009/0304245 | A1 | 12/2009 | Egger et al. | |
| 2010/0017171 | A1 | 1/2010 | Spilker | |
| 2010/0241404 | A1 | 9/2010 | Taylor et al. | |
| 2011/0071404 | A1 | 3/2011 | Schmitt et al. | |
| 2011/0153286 | A1 | 6/2011 | Zaeuner et al. | |
| 2012/0022843 | A1 | 1/2012 | Ionasec et al. | |
| 2012/0041318 | A1 | 2/2012 | Taylor | |
| 2012/0072190 | A1* | 3/2012 | Sharma | G06T 7/0016 703/2 |
| 2014/0114618 | A1* | 4/2014 | Fonte | G06T 19/00 703/1 |
| 2015/0302139 | A1* | 10/2015 | Sankaran | A61B 5/7275 703/20 |
| 2015/0374243 | A1* | 12/2015 | Itu | G16H 50/50 703/2 |
| 2016/0022371 | A1* | 1/2016 | Sauer | A61B 6/504 600/407 |
| 2016/0042145 | A1* | 2/2016 | Sankaran | G16H 50/30 703/11 |
| 2016/0148371 | A1* | 5/2016 | Itu | G16H 50/50 382/128 |
| 2018/0242857 | A1* | 8/2018 | Sharma | A61B 5/0261 |

OTHER PUBLICATIONS

Lesage, et al. "A Review of 3D Vessel Lumen Segmentation Techniques: Models, Features and Extraction Schemes." Medical Image Analysis 13, (2009): 819-45. Print.
Chen, et al. "Quantifying 3-D Vascular Structures in MRA Images Using Hybrid PDE and Geometric Deformable Models." IEEE Transactions on Medical Imaging 23.10 (2004): 1251-262. Print.
Pizaine, et al. "Vessel Geometry Modeling and Segmentation Using Convolution Surfaces and an Implicit Medial Axis." IEEE International Symposium on Biomedical Imaging: From Nano to Macro (2011): 1421-424. Print.
Buhler, et al. "Geometric Methods for Vessel Visualization and Quantification—A Survey." Geometric Modeling for Scientific Visualization (2004): 399-419. Print.
Florez-Valencia, et al. "3D Graphical Models for Vascular-stent Pose Simulation." ICCVG (2002): 1-8. Print.
Gijsen, et al. "Simulation of Stent Deployment in a Realistic Human Coronary Artery." BioMedical Engineering OnLine 7.23 (2008): 1-11. Print.
Mortier, et al. "A Novel Simulation Strategy for Stent Insertion and Deployment in Curved Coronary Bifurcations: Comparison of Three Drug-Eluting Stents." Annals of Biomedical Engineering 38.1 (2009): 88-99. Print.
Zelicourt, et al. "Imaging and patient-specific simulations for the Fontan surgery: Current methodologies and clinical application." Progress in Pediatric Cardiology. 30. (2010) 31-44. Print.
Hauskrecht et al. "Planning Treatment of Ischemic Heart Disease with Partially Observable Markov Decision Processes," Artificial Intelligence in Medicine. 18. (2000); 221-244 (cited as p. 1-20).
Hauskrecht et al. "Modeling Treatment of Ischemic heart Disease with Partially Observable Markov Decision Processes," Proc AMIA Symp. (1998): 538-542.
Taylor, et al. "Patient-Specific Modeling of Cardiovascular Mechanics." Annu. Rev. Biomed. Eng.. 11. (2009): 109-134. Print.
Nobile, F. "Coupling strategies for the numerical simulation of blood flow in deformable arteries by 3D and 1D models." Mathematical and Computer Modeling. 49. (2009): 2152-2160. Print.
Taylor, et al. "Predictive Medicine: Computational Techniques in Therapeutic Decision-Making." Computer Aided Surgery. 4. (1999): 231-247. Print.

(56) References Cited

OTHER PUBLICATIONS

International Search Report and Written Opinion for corresponding International Application No. PCT/US2014/018973 dated Jun. 25, 2014, (17 pages).
Piotr Kalita et al. "Mechanical Models of Artery Walls", Archives of Computational Methods in Engineering, vol. 15, No. 1, Mar. 1, 2008, pp. 3-36.
Draney, et al. "Predictive Medicine: Computational Techniques in Therapeutic Decision-Making." Computer Aided Surgery. 4. (1999): 231-247. Print.

\* cited by examiner

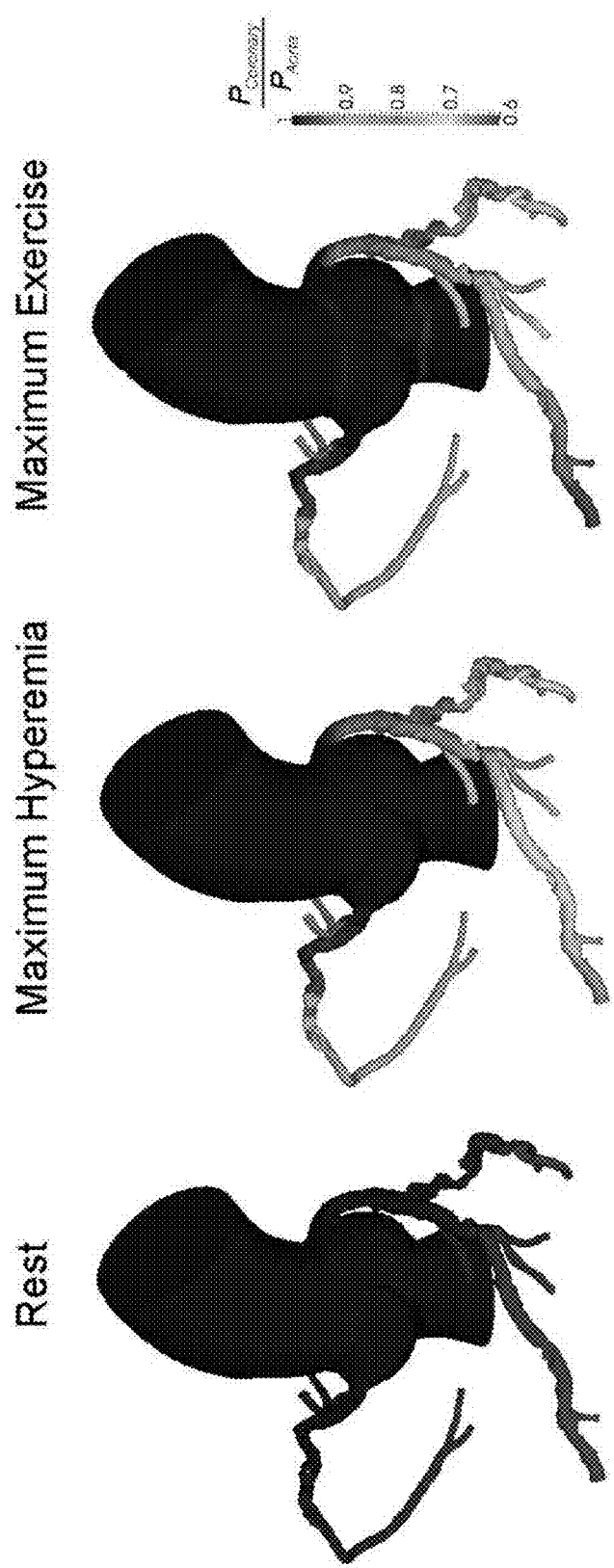

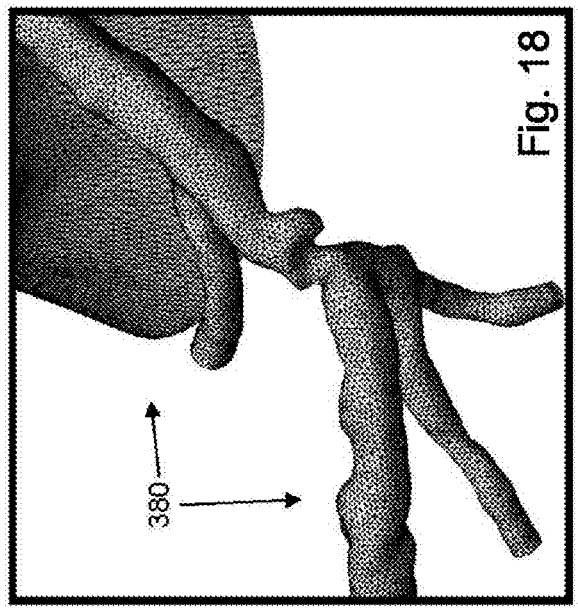
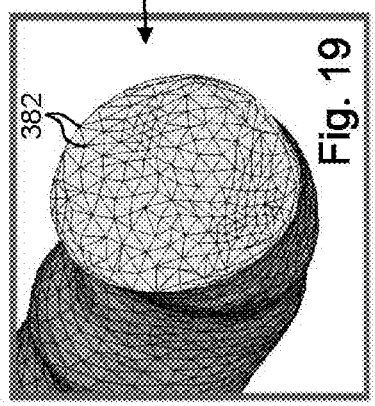
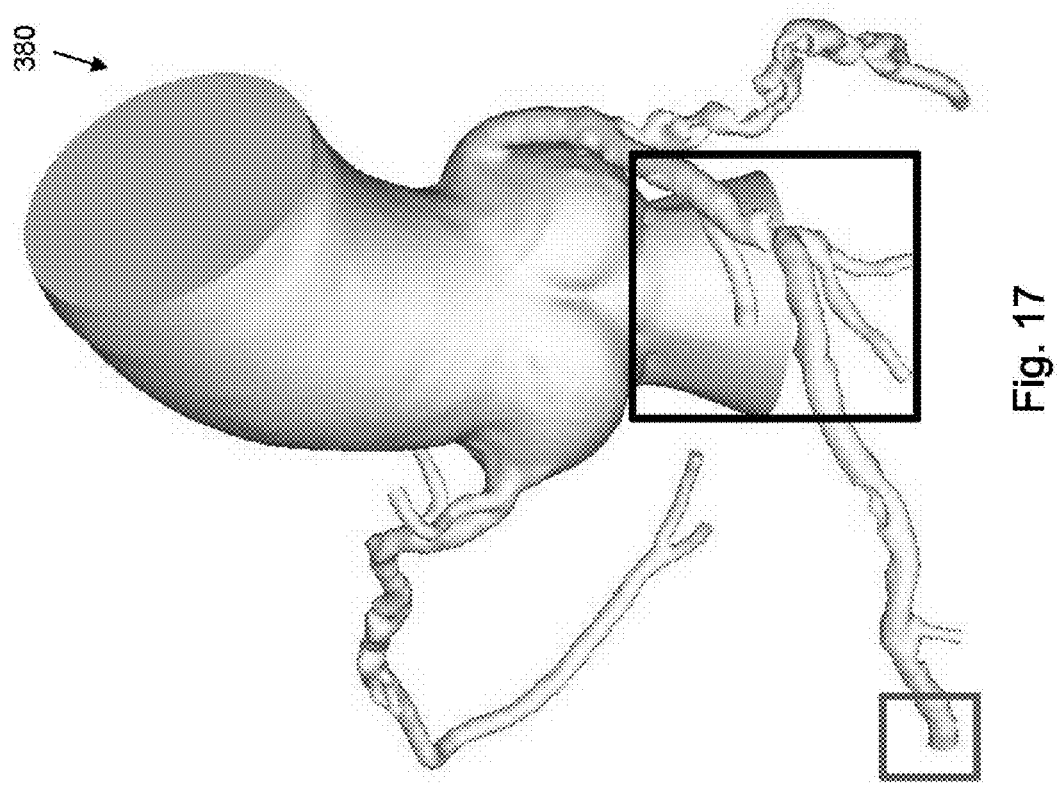

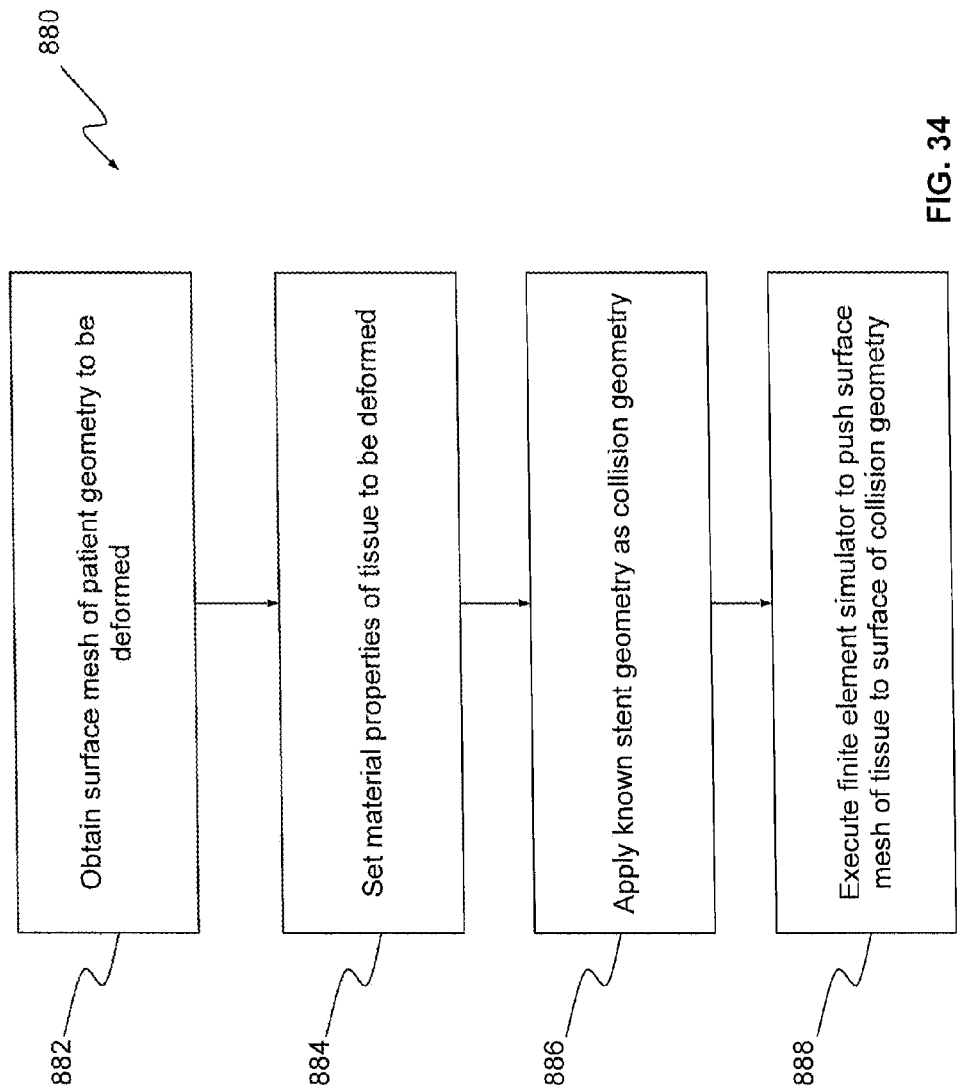

METHOD AND SYSTEM FOR DETERMINING TREATMENTS BY MODIFYING PATIENT-SPECIFIC GEOMETRICAL MODELS

CROSS REFERENCE TO RELATED APPLICATION

This application is a continuation of U.S. application Ser. No. 15/080,955, filed Mar. 25, 2016, which is a continuation of U.S. application Ser. No. 14/323,300, filed Jul. 3, 2014, which is a continuation of U.S. patent application Ser. No. 13/782,307, filed on Mar. 1, 2013, now U.S. Pat. No. 9,042,613, all of which are hereby incorporated herein by reference in their entireties.

TECHNICAL FIELD

Embodiments include methods and systems for determining patient treatment options, and more particularly, to methods and systems for determining treatment options by modifying patient-specific geometric models.

BACKGROUND

Coronary artery disease may produce coronary lesions in the blood vessels providing blood to the heart, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

A need exists to provide more accurate data relating to coronary lesions, e.g., size, shape, location, functional significance (e.g., whether the lesion impacts blood flow), etc. Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). These noninvasive tests, however, typically do not provide a direct assessment of coronary lesions or assess blood flow rates. The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers).

For example, anatomic data may be obtained noninvasively using coronary computed tomographic angiography (CCTA). CCTA may be used for imaging of patients with chest pain and involves using computed tomography (CT) technology to image the heart and the coronary arteries following an intravenous infusion of a contrast agent. However, CCTA also cannot provide direct information on the functional significance of coronary lesions, e.g., whether the lesions affect blood flow. In addition, since CCTA is purely a diagnostic test, it cannot be used to predict changes in coronary blood flow, pressure, or myocardial perfusion under other physiologic states, e.g., exercise, nor can it be used to predict outcomes of interventions.

Thus, patients may also require an invasive test, such as diagnostic cardiac catheterization, to visualize coronary lesions. Diagnostic cardiac catheterization may include performing conventional coronary angiography (CCA) to gather anatomic data on coronary lesions by providing a doctor with an image of the size and shape of the arteries. CCA, however, does not provide data for assessing the functional significance of coronary lesions. For example, a doctor may not be able to diagnose whether a coronary lesion is harmful without determining whether the lesion is functionally significant. Thus, CCA has led to what has been referred to as an "oculostenotic reflex" of some interventional cardiologists to insert a stent for every lesion found with CCA regardless of whether the lesion is functionally significant. As a result, CCA may lead to unnecessary operations on the patient, which may pose added risks to patients and may result in unnecessary heath care costs for patients.

During diagnostic cardiac catheterization, the functional significance of a coronary lesion may be assessed invasively by measuring the fractional flow reserve (FFR) of an observed lesion. FFR is defined as the ratio of the mean blood pressure downstream of a lesion divided by the mean blood pressure upstream from the lesion, e.g., the aortic pressure, under conditions of increased coronary blood flow, e.g., induced by intravenous administration of adenosine. The blood pressures may be measured by inserting a pressure wire into the patient. Thus, the decision to treat a lesion based on the determined FFR may be made after the initial cost and risk of diagnostic cardiac catheterization has already been incurred.

Thus, a need exists for a method for assessing coronary anatomy, myocardial perfusion, and coronary artery flow noninvasively. Such a method and system may benefit cardiologists who diagnose and plan treatments for patients with suspected coronary artery disease. In addition, a need exists for a method to predict coronary artery flow and myocardial perfusion under conditions that cannot be directly measured, e.g., exercise, and to predict outcomes of medical, interventional, and surgical treatments on coronary artery blood flow and myocardial perfusion.

In addition, a need exists to automatically identify an optimal treatment option from a plurality of feasible treatment options (e.g., all possible percutaneous coronary intervention (PCI) or coronary arterial bypass grafts (CABG) options), by analyzing noninvasively assessed coronary anatomy.

SUMMARY OF THE DISCLOSURE

In certain embodiments, systems are disclosed for evaluating cardiovascular treatment options for a patient. A system includes at least one computer system configured to: create a three-dimensional model representing at least a portion of the patient's heart or vasculature based on patient-specific data regarding a geometry of the patient's heart or vasculature; and for each of a plurality of treatment options for treating at least a portion of the patient's heart or vasculature, modify at least one of the three-dimensional model and a reduced order model based on the three-dimensional. The computer system is further configured to determine, for each of the plurality of treatment options, a value of a blood flow characteristic, by solving at least one of the modified three-dimensional model and the modified reduced order model; and identify one of the plurality of treatment options that solves a function of at least one of: the determined blood flow characteristics of the patient's heart or vasculature, and one or more costs of each of the plurality of treatment options.

In certain embodiments, the computer system is configured to modify, for each of the plurality of treatment options, the three-dimensional model using a geometric modification technique. The computer system is configured to modify, for each of the plurality of treatment options, the three-dimensional model using a constructive solid geometry union. The computer system is configured to modify, for each of the plurality of treatment options, the three-dimensional model using an elastic deformation modification technique. The computer system is configured to modify, for each of the plurality of treatment options, the three-dimensional model based on a simulated location of an inserted stent or bypass graft. The computer system is configured to modify the three-dimensional model for a subset of each of the plurality of treatment options in locations that exhibit a predetermined threshold level of a blood flow characteristic.

In certain embodiments, the computer system is configured to: create the reduced order model relating to a blood flow characteristic of the patient's heart or vasculature, based on the three-dimensional model; and modify the reduced order model for each possible treatment option, using a resistance value estimated to be associated with a type and location of the respective possible treatment option. The computer system is configured to determine resistance values associated with possible treatment options from historical data of known resistance values associated with a known dimension or geometry of previously implemented treatment options. The objective function is configured to maximize blood flow or minimize pressure changes in a patient's coronary vasculature. The objective function is configured to penalize one or more of: increasing numbers of stents or bypass grafts; decreasing of FFR values in larger vessels, as opposed to smaller vessels; increasing proximity of inserted stents; treatment costs; and the existence or number of bifurcations. The three-dimensional model representing at least the portion of the patient's heart includes at least a portion of an aorta and at least a portion of a plurality of coronary arteries emanating from the portion of the aorta.

In certain embodiments, the blood flow characteristic indicates a ratio between a pressure in the aorta and a pressure at a location in the plurality of coronary arteries; and the computer system is configured to determine the blood flow characteristic at a plurality of locations in the plurality of coronary arteries. The patient-specific data includes imaging data provided by computer tomography or magnetic resonance imaging techniques. The reduced order model includes at least one lumped parameter model representing a blood flow through boundaries of the three-dimensional model. The computer system is configured to determine the blood flow characteristic using a parameter associated with at least one of a level of hyperemia, a level of exercise, or a medication.

In certain embodiments, methods are disclosed for evaluating cardiovascular treatment options for a patient. One method includes creating a three-dimensional model representing at least a portion of the patient's heart or vasculature based on patient-specific data regarding a geometry of the patient's heart or vasculature; and for each of a plurality of treatment options for treating at least a portion of the patient's heart or vasculature, modifying at least one of the three-dimensional model and a reduced order model based on the three-dimensional model. The method also includes determining, for each of the plurality of treatment options, a value of a blood flow characteristic, by solving at least one of the modified three-dimensional model and the modified reduced order model; and identifying one of the plurality of treatment options that solves a function of at least one of: the determined blood flow characteristics of the patient's heart or vasculature, and one or more costs of each of the plurality of treatment options.

In certain embodiments, the method includes modifying, for each of the plurality of treatment options, the three-dimensional model using at least one of: a geometric modification technique; a constructive solid geometry union; and an elastic deformation modification technique. The method further includes modifying, for each of the plurality of treatment options, the three-dimensional model based on a simulated location of an inserted stent or bypass graft. The method further includes modifying the three-dimensional model for a subset of each of the plurality of treatment options in locations that exhibit a predetermined threshold level of a blood flow characteristic.

The method further includes creating the reduced order model relating to a blood flow characteristic of the patient's heart or vasculature, based on the three-dimensional model; and modifying the reduced order model for each possible treatment option, using a resistance value estimated to be associated with a type and location of the respective possible treatment option. The method further includes determining resistance values associated with possible treatment options from historical data of known resistance values associated with a known dimension or geometry of previously implemented treatment options.

The objective function is configured to maximize blood flow or minimize pressure changes in a patient's coronary vasculature. The objective function is configured to penalize one or more of: increasing numbers of stents or bypass grafts; decreasing of FFR values in larger vessels, as opposed to smaller vessels; increasing proximity of inserted stents; treatment costs; and the existence or number of bifurcations. the three-dimensional model representing at least the portion of the patient's heart includes at least a portion of an aorta and at least a portion of a plurality of coronary arteries emanating from the portion of the aorta. The blood flow characteristic indicates a ratio between a pressure in the aorta and a pressure at a location in the plurality of coronary arteries; and the computer system is configured to determine the blood flow characteristic at a plurality of locations in the plurality of coronary arteries.

The patient-specific data includes imaging data provided by computer tomography or magnetic resonance imaging techniques. The reduced order model includes at least one lumped parameter model representing a blood flow through boundaries of the three-dimensional model. The method further includes determining the blood flow characteristic using a parameter associated with at least one of a level of hyperemia, a level of exercise, or a medication.

The foregoing general description and the following detailed description are exemplary and explanatory only and are not restrictive of the disclosure.

Additional embodiments and advantages will be set forth in part in the description which follows, and in part will be obvious from the description, or may be learned by practice of the disclosure. The embodiments and advantages will be realized and attained by means of the elements and combinations particularly pointed out below.

BRIEF DESCRIPTION OF THE DRAWINGS

The accompanying drawings, which are incorporated in and constitute a part of this specification, illustrate several embodiments and together with the description, serve to explain the principles of the disclosure.

FIG. 9 shows an exemplary computed FFR (cFFR) model when the patient is at rest;

FIG. 10 shows an exemplary cFFR model when the patient is under maximum hyperemia;

FIG. 11 shows an exemplary cFFR model when the patient is under maximum exercise;

FIG. 17 shows a three-dimensional mesh prepared based on the solid model of FIG. 8;

FIGS. 18 and 19 show portions of the three-dimensional mesh of FIG. 17;

FIG. 34 depicts an exemplary method for performing an elastic deformation technique for modifying a patient-specific geometric model.

DESCRIPTION OF THE EMBODIMENTS

Figure 1:
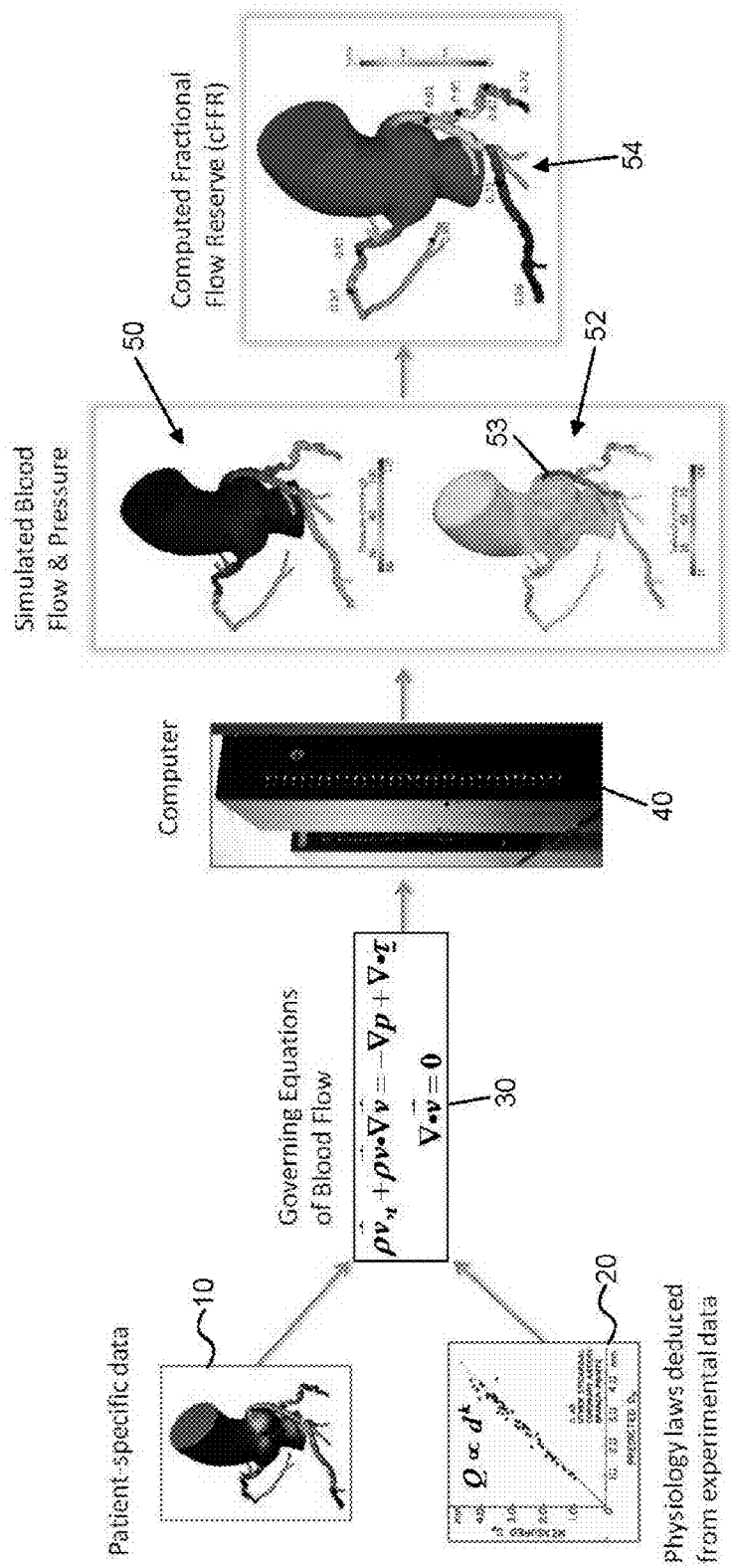
FIG. 1 is a schematic diagram of a system for providing various information relating to coronary blood flow in a specific patient, according to an exemplary embodiment.

Reference will now be made in detail to exemplary embodiments, examples of which are illustrated in the accompanying drawings. Wherever possible, the same reference numbers will be used throughout the drawings to refer to the same or like parts. This description is organized according to the following outline:

I. Overview
II. Obtaining and Preprocessing Patient-Specific Anatomical Data
III. Creating The Three-Dimensional Model Based On Obtained Anatomical Data
IV. Preparing The Model For Analysis and Determining Boundary Conditions
   A. Preparing the Model For Analysis
   B. Determining Boundary Conditions
      i. Determining Reduced Order Models
      ii. Exemplary Lumped Parameter Models
   C. Creating the Three-Dimensional Mesh
V. Performing The Computational Analysis And Outputting Results
   A. Performing the Computational Analysis
   B. Displaying Results for Blood Pressure, Flow, and cFFR
   C. Verifying Results
   D. Another Embodiment of a System and Method for Providing Coronary Blood Flow Information
VI. Providing Patient-Specific Treatment Planning
   A. Using Reduced Order Models to Compare Different Treatment Options
   B. Modifying Patient-Specific Geometrical Models to Optimize Treatment Options I. Overview In an exemplary embodiment, a method and system determines various information relating to blood flow in a specific patient using information retrieved from the patient noninvasively. The determined information may relate to blood flow in the patient's coronary vasculature. Alternatively, as will be described below in further detail, the determined information may relate to blood flow in other areas of the patient's vasculature, such as carotid, peripheral, abdominal, renal, and cerebral vasculature. The coronary vasculature includes a complex network of vessels ranging from large arteries to arterioles, capillaries, venules, veins, etc. The coronary vasculature circulates blood to and within the heart and includes an aorta 2 (FIG. 5) that supplies blood to a plurality of main coronary arteries 4 (FIG. 5) (e.g., the left anterior descending (LAD) artery, the left circumflex (LCX) artery, the right coronary (RCA) artery, etc.), which may further divide into branches of arteries or other types of vessels downstream from the aorta 2 and the main coronary arteries 4. Thus, the exemplary method and system may determine various information relating to blood flow within the aorta, the main coronary arteries, and/or other coronary arteries or vessels downstream from the main coronary arteries. Although the aorta and coronary arteries (and the branches that extend therefrom) are discussed below, the disclosed method and system may also apply to other types of vessels.

In an exemplary embodiment, the information determined by the disclosed methods and systems may include, but is not limited to, various blood flow characteristics or parameters, such as blood flow velocity, pressure (or a ratio thereof), flow rate, and FFR at various locations in the aorta, the main coronary arteries, and/or other coronary arteries or vessels downstream from the main coronary arteries. This information may be used to determine whether a lesion is functionally significant and/or whether to treat the lesion. This information may be determined using information obtained noninvasively from the patient. As a result, the decision whether to treat a lesion may be made without the cost and risk associated with invasive procedures.

FIG. 1 shows aspects of a system for providing various information relating to coronary blood flow in a specific patient, according to an exemplary embodiment. A three-dimensional model 10 of the patient's anatomy may be created using data obtained noninvasively from the patient as will be described below in more detail. Other patient-specific information may also be obtained noninvasively. In an exemplary embodiment, the portion of the patient's anatomy that is represented by the three-dimensional model 10 may include at least a portion of the aorta and a proximal portion of the main coronary arteries (and the branches extending or emanating therefrom) connected to the aorta.

Various physiological laws or relationships 20 relating to coronary blood flow may be deduced, e.g., from experimental data as will be described below in more detail. Using the three-dimensional anatomical model 10 and the deduced physiological laws 20, a plurality of equations 30 relating to coronary blood flow may be determined as will be described below in more detail. For example, the equations 30 may be determined and solved using any numerical method, e.g., finite difference, finite volume, spectral, lattice Boltzmann, particle-based, level set, finite element methods, etc. The equations 30 may be solvable to determine information (e.g., pressure, velocity, FFR, etc.) about the coronary blood flow in the patient's anatomy at various points in the anatomy represented by the model 10.

The equations 30 may be solved using a computer 40. Based on the solved equations, the computer 40 may output one or more images or simulations indicating information relating to the blood flow in the patient's anatomy represented by the model 10. For example, the image(s) may include a simulated blood pressure model 50, a simulated blood flow or velocity model 52, a computed FFR (cFFR) model 54, etc., as will be described in further detail below. The simulated blood pressure model 50, the simulated blood flow model 52, and the cFFR model 54 provide information regarding the respective pressure, velocity, and cFFR at various locations along three dimensions in the patient's anatomy represented by the model 10. cFFR may be calculated as the ratio of the blood pressure at a particular location in the model 10 divided by the blood pressure in the aorta, e.g., at the inflow boundary of the model 10, under conditions of increased coronary blood flow, e.g., conventionally induced by intravenous administration of adenosine.

In an exemplary embodiment, the computer 40 may include one or more non-transitory computer-readable storage devices that store instructions that, when executed by a processor, computer system, etc., may perform any of the actions described herein for providing various information relating to blood flow in the patient. The computer 40 may include a desktop or portable computer, a workstation, a server, a personal digital assistant, or any other computer system. The computer 40 may include a processor, a read-only memory (ROM), a random access memory (RAM), an input/output (I/O) adapter for connecting peripheral devices (e.g., an input device, output device, storage device, etc.), a user interface adapter for connecting input devices such as a keyboard, a mouse, a touch screen, a voice input, and/or other devices, a communications adapter for connecting the computer 40 to a network, a display adapter for connecting the computer 40 to a display, etc. For example, the display may be used to display the three-dimensional model 10 and/or any images generated by solving the equations 30, such as the simulated blood pressure model 50, the simulated blood flow model 52, and/or the cFFR model 54.

Figure 2:
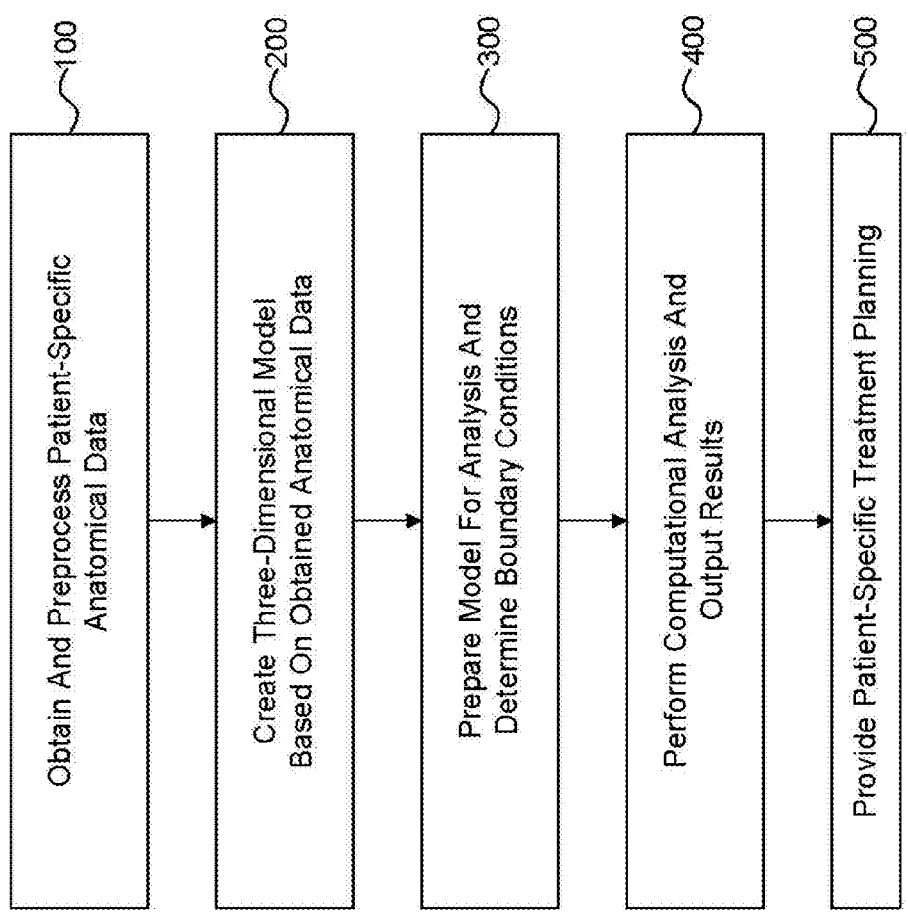
FIG. 2 is a flow chart of a method for providing various information relating to blood flow in a specific patient, according to an exemplary embodiment.

FIG. 2 shows aspects of a method for providing various information relating to blood flow in a specific patient, according to another exemplary embodiment. The method may include obtaining patient-specific anatomical data, such as information regarding the patient's anatomy (e.g., at least a portion of the aorta and a proximal portion of the main coronary arteries (and the branches extending therefrom) connected to the aorta), and preprocessing the data (step 100). The patient-specific anatomical data may be obtained noninvasively, e.g., by CCTA, as will be described below.

A three-dimensional model of the patient's anatomy may be created based on the obtained anatomical data (step 200). For example, the three-dimensional model may be the three-dimensional model 10 of the patient's anatomy described above in connection with FIG. 1.

The three-dimensional model may be prepared for analysis and boundary conditions may be determined (step 300). For example, the three-dimensional model 10 of the patient's anatomy described above in connection with FIG. 1 may be trimmed and discretized into a volumetric mesh, e.g., a finite element or finite volume mesh. The volumetric mesh may be used to generate the equations 30 described above in connection with FIG. 1.

Boundary conditions may also be assigned and incorporated into the equations 30 described above in connection with FIG. 1. The boundary conditions provide information about the three-dimensional model 10 at its boundaries, e.g., the inflow boundaries 322 (FIG. 8), the outflow boundaries 324 (FIG. 8), the vessel wall boundaries 326 (FIG. 8), etc. The inflow boundaries 322 may include the boundaries through which flow is directed into the anatomy of the three-dimensional model, such as at an end of the aorta near the aortic root (e.g., end A shown in FIG. 16). Each inflow boundary 322 may be assigned, e.g., with a prescribed value or field for velocity, flow rate, pressure, or other characteristic, by coupling a heart model and/or a lumped parameter model to the boundary, etc. The outflow boundaries 324 may include the boundaries through which flow is directed outward from the anatomy of the three-dimensional model, such as at an end of the aorta near the aortic arch (e.g., end B shown in FIG. 16), and the downstream ends of the main coronary arteries and the branches that extend therefrom (e.g., ends a-m shown in FIG. 16). Each outflow boundary can be assigned, e.g., by coupling a lumped parameter or distributed (e.g., a one-dimensional wave propagation) model, as will be described in detail below. The prescribed values for the inflow and/or outflow boundary conditions may be determined by noninvasively measuring physiologic characteristics of the patient, such as, but not limited to, cardiac output (the volume of blood flow from the heart), blood pressure, myocardial mass, etc. The vessel wall boundaries may include the physical boundaries of the aorta, the main coronary arteries, and/or other coronary arteries or vessels of the three-dimensional model 10.

The computational analysis may be performed using the prepared three-dimensional model and the determined boundary conditions (step 400) to determine blood flow information for the patient. For example, the computational analysis may be performed with the equations 30 and using the computer 40 described above in connection with FIG. 1 to produce the images described above in connection with FIG. 1, such as the simulated blood pressure model 50, the simulated blood flow model 52, and/or the cFFR model 54.

The method may also include providing patient-specific treatment options using the results (step 500). For example, the three-dimensional model 10 created in step 200 and/or the boundary conditions assigned in step 300 may be adjusted to model one or more treatments, e.g., placing a coronary stent in one of the coronary arteries represented in the three-dimensional model 10 or other treatment options. Then, the computational analysis may be performed as described above in step 400 in order to produce new images, such as updated versions of the blood pressure model 50, the blood flow model 52, and/or the cFFR model 54. These new images may be used to determine a change in blood flow velocity and pressure if the treatment option(s) are adopted.

The systems and methods disclosed herein may be incorporated into a software tool accessed by physicians to provide a noninvasive means to quantify blood flow in the coronary arteries and to assess the functional significance of coronary artery disease. In addition, physicians may use the software tool to predict the effect of medical, interventional, and/or surgical treatments on coronary artery blood flow. The software tool may prevent, diagnose, manage, and/or treat disease in other portions of the cardiovascular system including arteries of the neck (e.g., carotid arteries), arteries in the head (e.g., cerebral arteries), arteries in the thorax, arteries in the abdomen (e.g., the abdominal aorta and its branches), arteries in the arms, or arteries in the legs (e.g., the femoral and popliteal arteries). The software tool may be interactive to enable physicians to develop optimal personalized therapies for patients.

For example, the software tool may be incorporated at least partially into a computer system, e.g., the computer 40 shown in FIG. 1 used by a physician or other user. The computer system may receive data obtained noninvasively from the patient (e.g., data used to create the three-dimensional model 10, data used to apply boundary conditions or perform the computational analysis, etc.). For example, the data may be input by the physician or may be received from another source capable of accessing and providing such data, such as a radiology or other medical lab. The data may be transmitted via a network or other system for communicating the data, or directly into the computer system. The software tool may use the data to produce and display the three-dimensional model 10 or other models/meshes and/or any simulations or other results determined by solving the equations 30 described above in connection with FIG. 1, such as the simulated blood pressure model 50, the simulated blood flow model 52, and/or the cFFR model 54. Thus, the software tool may perform steps 100-500. In step 500, the physician may provide further inputs to the computer system to select possible treatment options, and the computer system may display to the physician new simulations based on the selected possible treatment options. Further, each of steps 100-500 shown in FIG. 2 may be performed using separate software packages or modules.

Alternatively, the software tool may be provided as part of a web-based service or other service, e.g., a service provided by an entity that is separate from the physician. The service provider may, for example, operate the web-based service and may provide a web portal or other web-based application (e.g., run on a server or other computer system operated by the service provider) that is accessible to physicians or other users via a network or other methods of communicating data between computer systems. For example, the data obtained noninvasively from the patient may be provided to the service provider, and the service provider may use the data to produce the three-dimensional model 10 or other models/meshes and/or any simulations or other results determined by solving the equations 30 described above in connection with FIG. 1, such as the simulated blood pressure model 50, the simulated blood flow model 52, and/or the cFFR model 54. Then, the web-based service may transmit information relating to the three-dimensional model 10 or other models/meshes and/or the simulations so that the three-dimensional model 10 and/or the simulations may be displayed to the physician on the physician's computer system. Thus, the web-based service may perform steps 100-500 and any other steps described below for providing patient-specific information. In step 500, the physician may provide further inputs, e.g., to select possible treatment options or make other adjustments to the computational analysis, and the inputs may be transmitted to the computer system operated by the service provider (e.g., via the web portal). The web-based service may produce new simulations or other results based on the selected possible treatment options, and may communicate information relating to the new simulations back to the physician so that the new simulations may be displayed to the physician.

One or more of the steps described herein may be performed by one or more human operators (e.g., a cardiologist or other physician, the patient, an employee of the service provider providing the web-based service or other service provided by a third party, other user, etc.), or one or more computer systems used by such human operator(s), such as a desktop or portable computer, a workstation, a server, a personal digital assistant, etc. The computer system(s) may be connected via a network or other method of communicating data.

Figure 3:
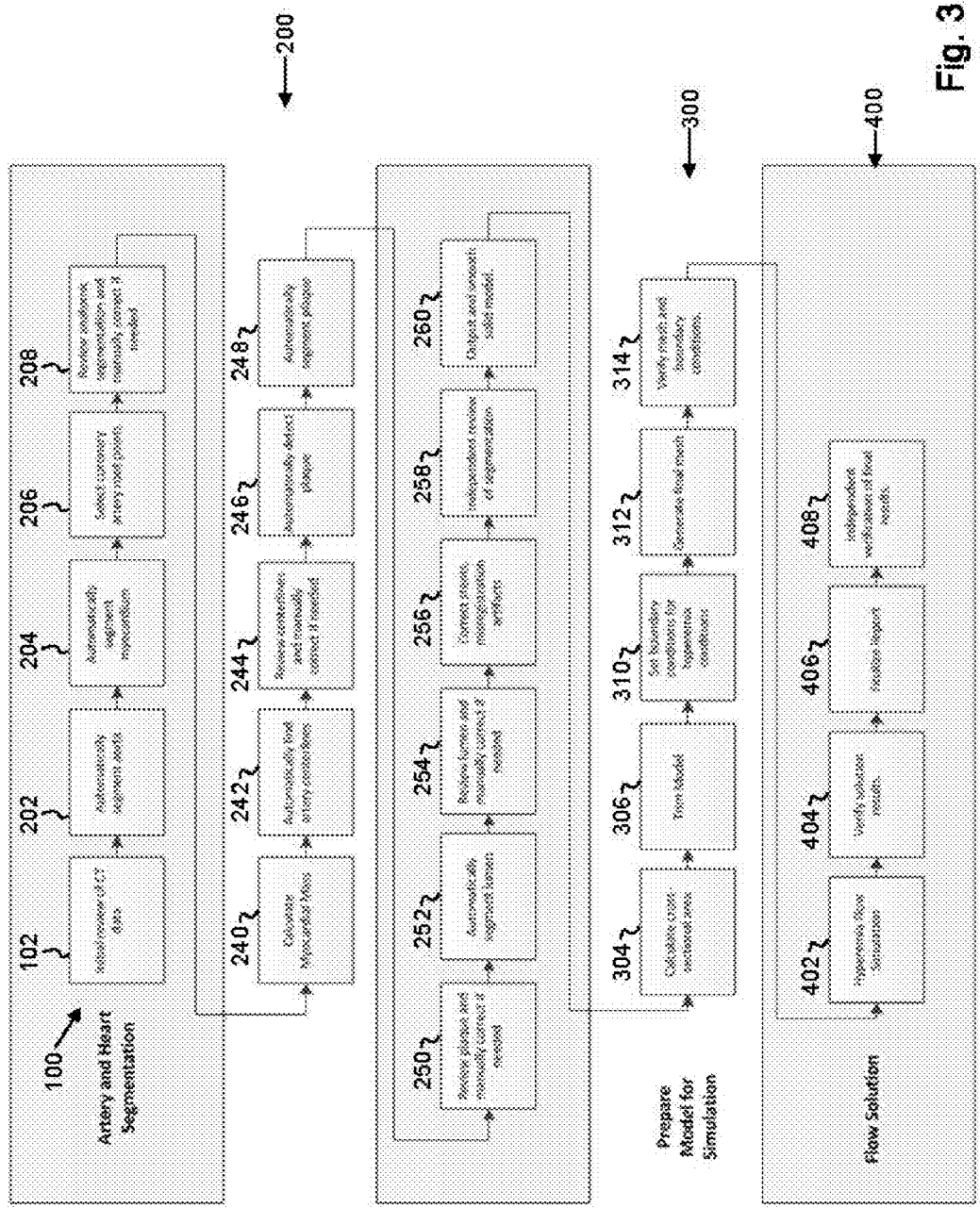
FIG. 3 is a flow chart showing the substeps of the method of FIG. 2.

FIG. 3 shows further aspects of the exemplary method for providing various information relating to blood flow in a specific patient. The aspects shown in FIG. 3 may be incorporated into the software tool that may be incorporated at least partially into a computer system and/or as part of a web-based service.

II. Obtaining and Preprocessing Patient-Specific Anatomical Data

As described above in connection with step 100 shown in FIG. 2, the exemplary method may include obtaining patient-specific anatomical data, such as information regarding the patient's heart, and preprocessing the data. In an exemplary embodiment, step 100 may include the following steps.

Initially, a patient may be selected. For example, the patient may be selected by the physician when the physician determines that information about the patient's coronary blood flow is desired, e.g., if the patient is experiencing symptoms associated with coronary artery disease, such as chest pain, heart attack, etc.

Figure 4:
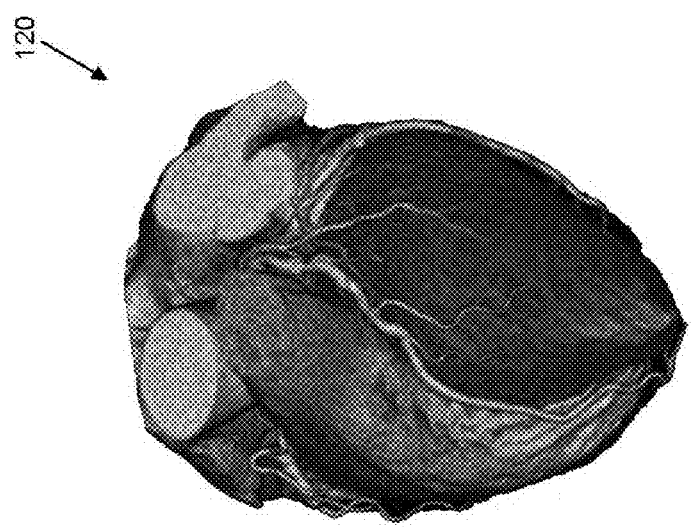
FIG. 4 shows imaging data obtained noninvasively from a patient, according to an exemplary embodiment.

Patient-specific anatomical data may be obtained, such as data regarding the geometry of the patient's heart, e.g., at least a portion of the patient's aorta, a proximal portion of the main coronary arteries (and the branches extending therefrom) connected to the aorta, and the myocardium. The patient-specific anatomical data may be obtained noninvasively, e.g., using a noninvasive imaging method. For example, CCTA is an imaging method in which a user may operate a computer tomography (CT) scanner to view and create images of structures, e.g., the myocardium, the aorta, the main coronary arteries, and other blood vessels connected thereto. The CCTA data may be time-varying, e.g., to show changes in vessel shape over a cardiac cycle. CCTA may be used to produce an image of the patient's heart. For example, 64-slice CCTA data may be obtained, e.g., data relating to 64 slices of the patient's heart, and assembled into a three-dimensional image. FIG. 4 shows an example of a three-dimensional image 120 produced by the 64-slice CCTA data.

Alternatively, other noninvasive imaging methods, such as magnetic resonance imaging (MRI) or ultrasound (US), or invasive imaging methods, such as digital subtraction angiography (DSA), may be used to produce images of the structures of the patient's anatomy. The imaging methods may involve injecting the patient intravenously with a contrast agent to enable identification of the structures of the anatomy. The resulting imaging data (e.g., provided by CCTA, MRI, etc.) may be provided by a third-party vendor, such as a radiology lab or a cardiologist, by the patient's physician, etc.

Other patient-specific anatomical data may also be determined from the patient noninvasively. For example, physiological data such as the patient's blood pressure, baseline heart rate, height, weight, hematocrit, stroke volume, etc., may be measured. The blood pressure may be the blood pressure in the patient's brachial artery (e.g., using a pressure cuff), such as the maximum (systolic) and minimum (diastolic) pressures.

The patient-specific anatomical data obtained as described above may be transferred over a secure communication line (e.g., via a network). For example, the data may be transferred to a server or other computer system for performing the computational analysis, e.g., the computational analysis described above in step 400. In an exemplary embodiment, the data may be transferred to a server or other computer system operated by a service provider providing a web-based service. Alternatively, the data may be transferred to a computer system operated by the patient's physician or other user.

Referring back to FIG. 3, the transferred data may be reviewed to determine if the data is acceptable (step 102). The determination may be performed by the user and/or by the computer system. For example, the transferred data (e.g., the CCTA data and other data) may be verified by a user and/or by the computer system, e.g., to determine if the CCTA data is complete (e.g., includes sufficient portions of the aorta and the main coronary arteries) and corresponds to the correct patient.

The transferred data (e.g., the CCTA data and other data) may also be preprocessed and assessed. The preprocessing and/or assessment may be performed by a user and/or by the computer system and may include, e.g., checking for misregistration, inconsistencies, or blurring in the CCTA data, checking for stents shown in the CCTA data, checking for other artifacts that may prevent the visibility of lumens of the blood vessels, checking for sufficient contrast between the structures (e.g., the aorta, the main coronary arteries, and other blood vessels) and the other portions of the patient, etc.

The transferred data may be evaluated to determine if the data is acceptable based on the verification, preprocessing, and/or assessment described above. During the verification, preprocessing, and/or assessment described above, the user and/or computer system may be able to correct certain errors or problems with the data. If, however, there are too many errors or problems, then the data may be determined to be unacceptable, and the user and/or computer system may generate a rejection report explaining the errors or problems necessitating the rejection of the transferred data. Optionally, a new CCTA scan may be performed and/or the physiological data described above may be measured from the patient again. If the transferred data is determined to be acceptable, then the method may proceed to step 202 described below.

Accordingly, step 102 shown in FIG. 3 and described above may be considered as a substep of step 100 of FIG. 2.

III. Creating the Three-Dimensional Model Based on Obtained Anatomical Data

As described above in connection with step 200 shown in FIG. 2, the exemplary method may include creating the three-dimensional model based on the obtained anatomical data. In an exemplary embodiment, step 200 may include the following steps.

Figure 5:
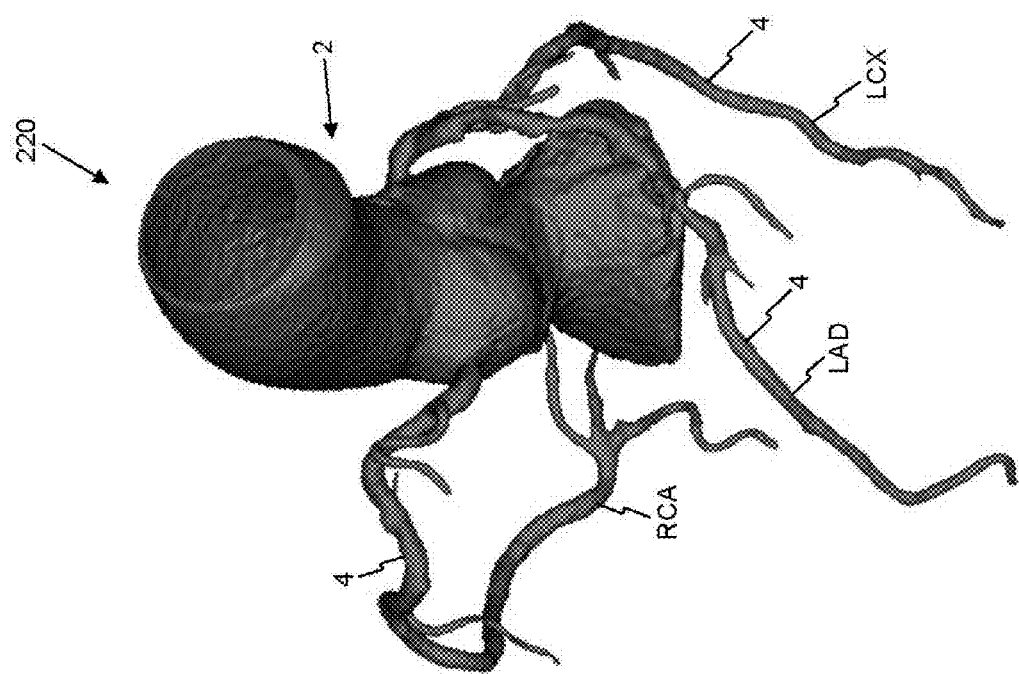
FIG. 5 shows an exemplary three-dimensional model generated using the imaging data of FIG. 4.

Using the CCTA data, a three-dimensional model of the coronary vessels may be generated. FIG. 5 shows an example of the surface of a three-dimensional model 220 generated using the CCTA data. For example, the model 220 may include, e.g., at least a portion of the aorta, at least a proximal portion of one or more main coronary arteries connected to that portion of the aorta, at least a proximal portion of one or more branches connected to the main coronary arteries, etc. The modeled portions of the aorta, the main coronary arteries, and/or the branches may be interconnected and treelike such that no portion is disconnected from the rest of the model 220. The process of forming the model 220 is called segmentation.

Referring back to FIG. 3, the computer system may automatically segment at least a portion of the aorta (step 202) and the myocardium (or other heart tissue, or other tissue connected to the arteries to be modeled) (step 204). The computer system may also segment at least a portion of the main coronary arteries connected to the aorta. In an exemplary embodiment, the computer system may allow the user to select one or more coronary artery root or starting points (step 206) in order to segment the main coronary arteries.

Segmentation may be performed using various methods. Segmentation may be performed automatically by the computer system based on user inputs or without user inputs. For example, in an exemplary embodiment, the user may provide inputs to the computer system in order to generate a first initial model. For example, the computer system may display to the user the three-dimensional image 120 (FIG. 4) or slices thereof produced from the CCTA data. The three-dimensional image 120 may include portions of varying intensity of lightness. For example, lighter areas may indicate the lumens of the aorta, the main coronary arteries, and/or the branches. Darker areas may indicate the myocardium and other tissue of the patient's heart.

Figure 6:
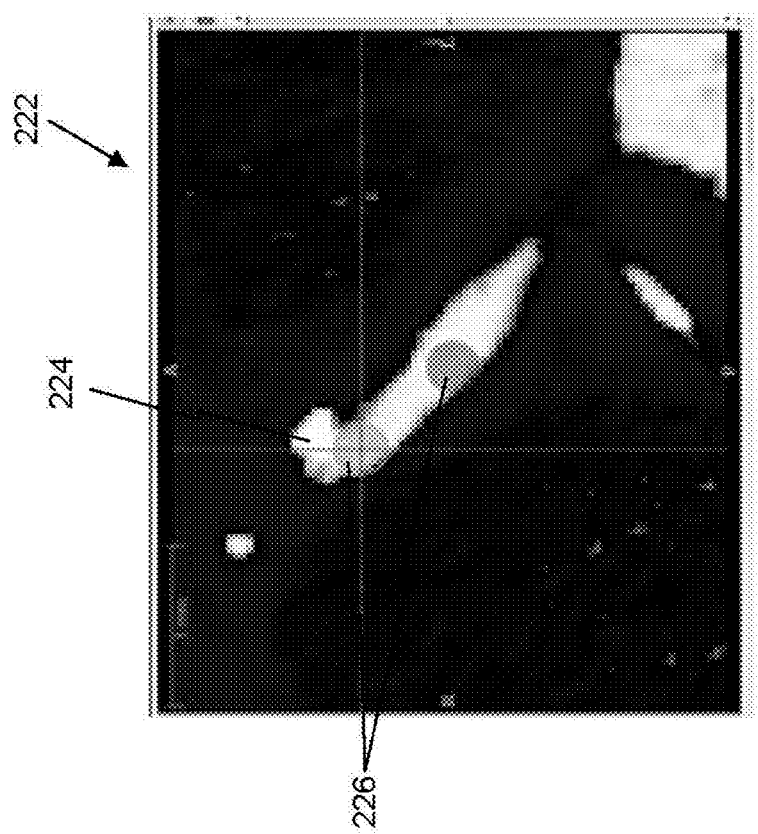
FIG. 6 shows a portion of a slice of the imaging data of FIG. 4 including seeds for forming a first initial model.

FIG. 6 shows a portion of a slice 222 of the three-dimensional image 120 that may be displayed to the user, and the slice 222 may include an area 224 of relative lightness. The computer system may allow the user to select the area 224 of relative lightness by adding one or more seeds 226, and the seeds 226 may serve as coronary artery root or starting points for segmenting the main coronary arteries. At the command of the user, the computer system may then use the seeds 226 as starting points to form the first initial model. The user may add seeds 226 in one or more of the aorta and/or the individual main coronary arteries. Optionally, the user may also add seeds 226 in one or more of the branches connected to the main coronary arteries. Alternatively, the computer system may place the seeds automatically, e.g., using extracted centerline information. The computer system may determine an intensity value of the image 120 where the seeds 226 have been placed and may form the first initial model by expanding the seeds 226 along the portions of the image 120 having the same intensity value (or within a range or threshold of intensity values centered at the selected intensity value). Thus, this method of segmentation may be called "threshold-based segmentation."

Figure 7:
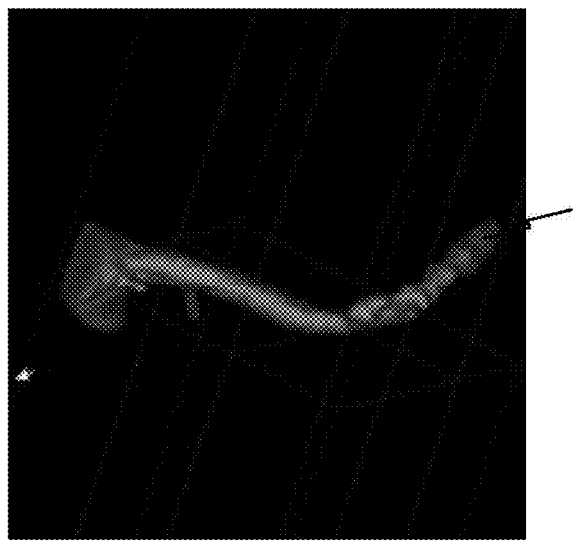
FIG. 7 shows a portion of the first initial model formed by expanding the seeds of FIG. 6.

FIG. 7 shows a portion 230 of the first initial model that is formed by expanding the seeds 226 of FIG. 6. Accordingly, the user inputs the seeds 226 as starting points for the computer system to begin forming the first initial model. This process may be repeated until the entire portions of interest, e.g., the portions of the aorta and/or the main coronary arteries, are segmented. Alternatively, the first initial model may be generated by the computer system without user inputs.

Alternatively, segmentation may be performed using a method called "edge-based segmentation." In an exemplary embodiment, both the threshold-based and edge-based segmentation methods may be performed, as will be described below, to form the model 220.

A second initial model may be formed using the edge-based segmentation method. With this method, the lumen edges of the aorta and/or the main coronary arteries may be located. For example, in an exemplary embodiment, the user may provide inputs to the computer system, e.g., the seeds 226 as described above, in order to generate the second initial model. The computer system may expand the seeds 226 along the portions of the image 120 until the edges are reached. The lumen edges may be located, e.g., by the user visually, and/or by the computer system (e.g., at locations where there is a change in intensity value above a set threshold). The edge-based segmentation method may be performed by the computer system and/or the user.

The myocardium or other tissue may also be segmented based on the CCTA data in step 204. For example, the CCTA data may be analyzed to determine the location of the internal and external surfaces of the myocardium, e.g., the left and/or right ventricles. The locations of the surfaces may be determined based on the contrast (e.g., relative darkness and lightness) of the myocardium compared to other structures of the heart in the CCTA data. Thus, the geometry of the myocardium may be determined.

The segmentation of the aorta, the myocardium, and/or the main coronary arteries may be reviewed and/or corrected, if necessary (step 208). The review and/or correction may be performed by the computer system and/or the user. For example, in an exemplary embodiment, the computer system may automatically review the segmentation, and the user may manually correct the segmentation if there are any errors, e.g., if any portions of the aorta, the myocardium, and/or the main coronary arteries in the model 220 are missing or inaccurate.

For example, the first and second initial models described above may be compared to ensure that the segmentation of the aorta and/or the main coronary arteries is accurate. Any areas of discrepancy between the first and second initial models may be compared to correct the segmentation and to form the model 220. For example, the model 220 may be an average between the first and second initial models. Alternatively, only one of the segmentation methods described above may be performed, and the initial model formed by that method may be used as the model 220.

The myocardial mass may be calculated (step 240). The calculation may be performed by the computer system. For example, the myocardial volume may be calculated based on the locations of the surfaces of the myocardium determined as described above, and the calculated myocardial volume may be multiplied by the density of the myocardium to calculate the myocardial mass. The density of the myocardium may be preset.

The centerlines of the various vessels (e.g., the aorta, the main coronary arteries, etc.) of the model 220 (FIG. 5) may be determined (step 242). In an exemplary embodiment, the determination may be performed automatically by the computer system.

The centerlines determined in step 242 may be reviewed and/or corrected, if necessary (step 244). The review and/or correction may be performed by the computer system and/or the user. For example, in an exemplary embodiment, the computer system may automatically review the centerlines, and the user may manually correct the centerlines if there are any errors, e.g., if any centerlines are missing or inaccurate.

Calcium or plaque (causing narrowing of a vessel) may be detected (step 246). In an exemplary embodiment, the computer system may automatically detect the plaque. For example, the plaque may be detected in the three-dimensional image 120 and removed from the model 220. The plaque may be identified in the three-dimensional image 120 since the plaque appears as areas that are even lighter than the lumens of the aorta, the main coronary arteries, and/or the branches. Thus, the plaque may be detected by the computer system as having an intensity value below a set value or may be detected visually by the user. After detecting the plaque, the computer system may remove the plaque from the model 220 so that the plaque is not considered as part of the lumen or open space in the vessels. Alternatively, the computer system may indicate the plaque on the model 220 using a different color, shading, or other visual indicator than the aorta, the main coronary arteries, and/or the branches.

The computer system may also automatically segment the detected plaque (step 248). For example, the plaque may be segmented based on the CCTA data. The CCTA data may be analyzed to locate the plaque (or a surface thereof) based on the contrast (e.g., relative darkness and lightness) of the plaque compared to other structures of the heart in the CCTA data. Thus, the geometry of the plaque may also be determined.

The segmentation of the plaque may be reviewed and/or corrected, if necessary (step 250). The review and/or correction may be performed by the computer system and/or the user. For example, in an exemplary embodiment, the computer system may automatically review the segmentation, and the user may manually correct the segmentation if there are any errors, e.g., if any plaque is missing or shown inaccurately.

The computer system may automatically segment the branches connected to the main coronary arteries (step 252). For example, the branches may be segmented using similar methods for segmenting the main coronary arteries, e.g., as shown in FIGS. 6 and 7 and described above in connection with step 206. The computer system may also automatically segment the plaque in the segmented branches using similar methods as described above in connection with steps 248 and 250. Alternatively, the branches (and any plaque contained therein) may be segmented at the same time as the main coronary arteries (e.g., in step 206).

The segmentation of the branches may be reviewed and/or corrected, if necessary (step 254). The review and/or correction may be performed by the computer system and/or the user. For example, in an exemplary embodiment, the computer system may automatically review the segmentation, and the user may manually correct the segmentation if there are any errors, e.g., if any portions of the branches in the model 220 are missing or inaccurate.

The model 220 may be corrected if any misregistration, stents, or other artifacts are located (e.g., during the review of the CCTA data in step 102) (step 256). The correction may be performed by a user and/or by the computer system. For example, if a misregistration or other artifact (e.g., inconsistency, blurring, an artifact affecting lumen visibility, etc.) is located, the model 220 may be reviewed and/or corrected to avoid an artificial or false change in the cross-sectional area of a vessel (e.g., an artificial narrowing). If a stent is located, the model 220 may be reviewed and/or corrected to indicate the location of the stent and/or to correct the cross-sectional area of the vessel where the stent is located, e.g., based on the size of the stent.

The segmentation of the model 220 may also be independently reviewed (step 258). The review may be performed by a user and/or by the computer system. For example, the user and/or computer system may be able to identify certain errors with the model 220, such as correctable errors and/or errors that may require the model 220 to be at least partially redone or resegmented. If such errors are identified, then the segmentation may be determined to be unacceptable, and certain steps, e.g., one or more of steps 202-208, 240-256, depending on the error(s), may be repeated.

If the segmentation of the model 220 is independently verified as acceptable, then, optionally, the model 220 may be output and smoothed (step 260). The smoothing may be performed by the user and/or by the computer system. For example, ridges, points, or other discontinuous portions may be smoothed. The model 220 may be output to a separate software module to be prepared for computational analysis, etc.

Accordingly, steps 202-208 and 240-260 shown in FIG. 3 and described above may be considered as substeps of step 200 of FIG. 2.

IV. Preparing the Model for Analysis and Determining Boundary Conditions

As described above in connection with step 300 shown in FIG. 2, the exemplary method may include preparing the model for analysis and determining boundary conditions. In an exemplary embodiment, step 300 may include the following steps.

A. Preparing the Model for Analysis

Referring back to FIG. 3, the cross-sectional areas of the various vessels (e.g., the aorta, the main coronary arteries, and/or the branches) of the model 220 (FIG. 5) may also be determined (step 304). In an exemplary embodiment, the determination may be performed by the computer system.

Figure 8:
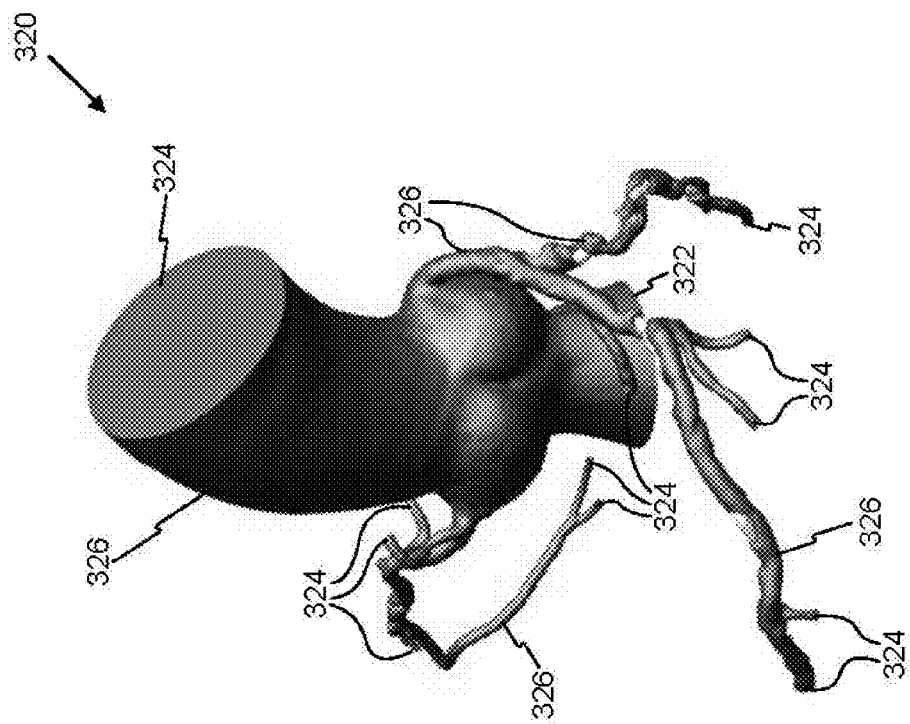
FIG. 8 shows a trimmed solid model, according to an exemplary embodiment.

The model 220 (FIG. 5) may be trimmed (step 306) and a solid model may be generated. FIG. 8 shows an example of the trimmed solid model 320 prepared based on a model similar to the model 220 shown in FIG. 5. The solid model 320 is a three-dimensional patient-specific geometric model. In an exemplary embodiment, the trimming may be performed by the computer system, with or without a user's input. Each of the inflow boundaries 322 and outflow boundaries 324 may be trimmed such that the surface forming the respective boundary is perpendicular to the centerlines determined in step 242. The inflow boundaries 322 may include the boundaries through which flow is directed into the anatomy of the model 320, such as at an upstream end of the aorta, as shown in FIG. 8. The outflow boundaries 324 may include the boundaries through which flow is directed outward from the anatomy of the model 320, such as at a downstream end of the aorta and the downstream ends of the main coronary arteries and/or branches.

B. Determining Boundary Conditions

Boundary conditions may be provided to describe what is occurring at the boundaries of the model, e.g., the three-dimensional solid model 320 of FIG. 8. For example, the boundary conditions may relate to at least one blood flow characteristic associated with the patient's modeled anatomy, e.g., at the boundaries of the modeled anatomy, and the blood flow characteristic(s) may include blood flow velocity, pressure, flow rate, FFR, etc. By appropriately determining the boundary conditions, a computational analysis may be performed to determine information at various locations within the model. Examples of boundary conditions and methods for determining such boundary conditions will now be described.

In an exemplary embodiment, the determined boundary conditions may simplify the structures upstream and downstream from the portions of the vessels represented by the solid model 320 into a one- or two-dimensional reduced order model. An exemplary set of equations and other details for determining the boundary conditions are disclosed, for example, in U.S. Patent Application Publication No. 2010/0241404 and U.S. Provisional Application No. 61/210,401, which are both entitled "Patient-Specific Hemodynamics of the Cardiovascular System" and hereby incorporated by reference in their entirety.

Boundary conditions may vary depending on the physiological condition of the patient since blood flow though the heart may differ depending on the physiological condition of the patient. For example, FFR is typically measured under the physiological condition of hyperemia, which generally occurs when the patient is experiencing increased blood flow in the heart, e.g., due to stress, etc. The FFR is the ratio of the coronary pressure to aortic pressure under conditions of maximum stress. Hyperemia may also be induced pharmacologically, e.g., with adenosine. FIGS. 9-11 show examples of a calculated FFR (cFFR) model that indicates the change in the ratio of coronary pressure to aortic pressure in the model 320, depending on the physiological condition of the patient (at rest, under maximum hyperemia, or under maximum exercise). FIG. 9 shows minimal variation in the ratio of coronary pressure to aortic pressure throughout the model 320 when the patient is at rest. FIG. 10 shows greater variation in the ratio of coronary pressure to aortic pressure throughout the model 320 when the patient is undergoing maximum hyperemia. FIG. 11 shows even greater variation in the ratio of coronary pressure to aortic pressure throughout the model 320 when the patient is undergoing maximum exercise.

Referring back to FIG. 3, boundary conditions for hyperemia conditions may be determined (step 310). In an exemplary embodiment, the effect of adenosine may be modeled using a decrease in coronary artery resistance by a factor of 1-5 fold, a decrease in aortic blood pressure of approximately 0-20%, and an increase in heart rate of approximately 0-20%. For example, the effect of adenosine may be modeled using a decrease in coronary artery resistance by a factor of 4 fold, a decrease in aortic blood pressure of approximately 10%, and an increase in heart rate of approximately 10%. Although the boundary conditions for hyperemia conditions are determined in the exemplary embodiment, it is understood that boundary conditions for other physiological states, such as rest, varying degrees of hyperemia, varying degrees of exercise, exertion, stress, or other conditions, may be determined.

Boundary conditions provide information about the three-dimensional solid model 320 at its boundaries, e.g., the inflow boundaries 322, the outflow boundaries 324, vessel wall boundaries 326, etc., as shown in FIG. 8. The vessel wall boundaries 326 may include the physical boundaries of the aorta, the main coronary arteries, and/or other coronary arteries or vessels of the model 320.

Each inflow or outflow boundary 322, 324 may be assigned a prescribed value or field of values for velocity, flow rate, pressure, or other blood flow characteristic. Alternatively, each inflow or outflow boundary 322, 324 may be assigned by coupling a heart model to the boundary, a lumped parameter or distributed (e.g. one-dimensional wave propagation) model, another type of one- or two-dimensional model, or other type of model. The specific boundary conditions may be determined based on, e.g., the geometry of the inflow or outflow boundaries 322, 324 determined from the obtained patient-specific information, or other measured parameters, such as cardiac output, blood pressure, the myocardial mass calculated in step 240, etc.

i. Determining Reduced Order Models

The upstream and downstream structures connected to the solid model 320 may be represented as reduced order models representing the upstream and downstream structures. For example, FIGS. 12-15 show aspects of a method for preparing a lumped parameter model from three-dimensional patient-specific anatomical data at one of the outflow boundaries 324, according to an exemplary embodiment. The method may be performed separately from and prior to the methods shown in FIGS. 2 and 3.

Figure 13:
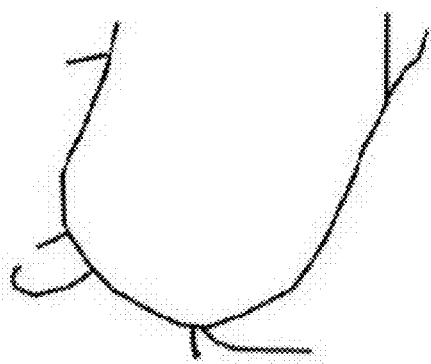
FIG. 13 shows a portion of the centerlines for the trimmed solid model of FIG. 12, provided for forming a lumped parameter model.
Figure 12:
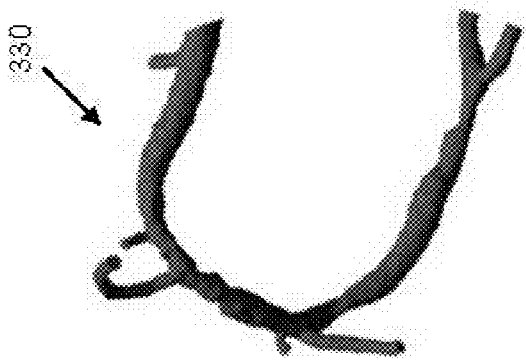
FIG. 12 shows a portion of a trimmed solid model provided for forming a lumped parameter model, according to an exemplary embodiment.

FIG. 12 shows a portion 330 of the solid model 320 of one of the main coronary arteries or the branches extending therefrom, and FIG. 13 shows the portion of the centerlines determined in step 242 of the portion 330 shown in FIG. 12.

Figure 14:
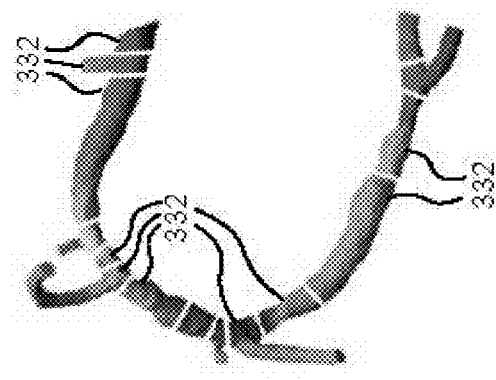
FIG. 14 shows segments formed based on the trimmed solid model of FIG. 12, provided for forming a lumped parameter model.

The portion 330 may be divided into segments 332. FIG. 14 shows an example of the segments 332 that may be formed from the portion 330. The selection of the lengths of the segments 332 may be performed by the user and/or the computer system. The segments 332 may vary in length, depending, for example, on the geometry of the segments 332. Various techniques may be used to segment the portion 330. For example, diseased portions, e.g., portions with a relatively narrow cross-section, a lesion, and/or a stenosis (an abnormal narrowing in a blood vessel), may be provided in one or more separate segments 332. The diseased portions and stenoses may be identified, e.g., by measuring the cross-sectional area along the length of the centerline and calculating locally minimum cross-sectional areas.

Figure 15:
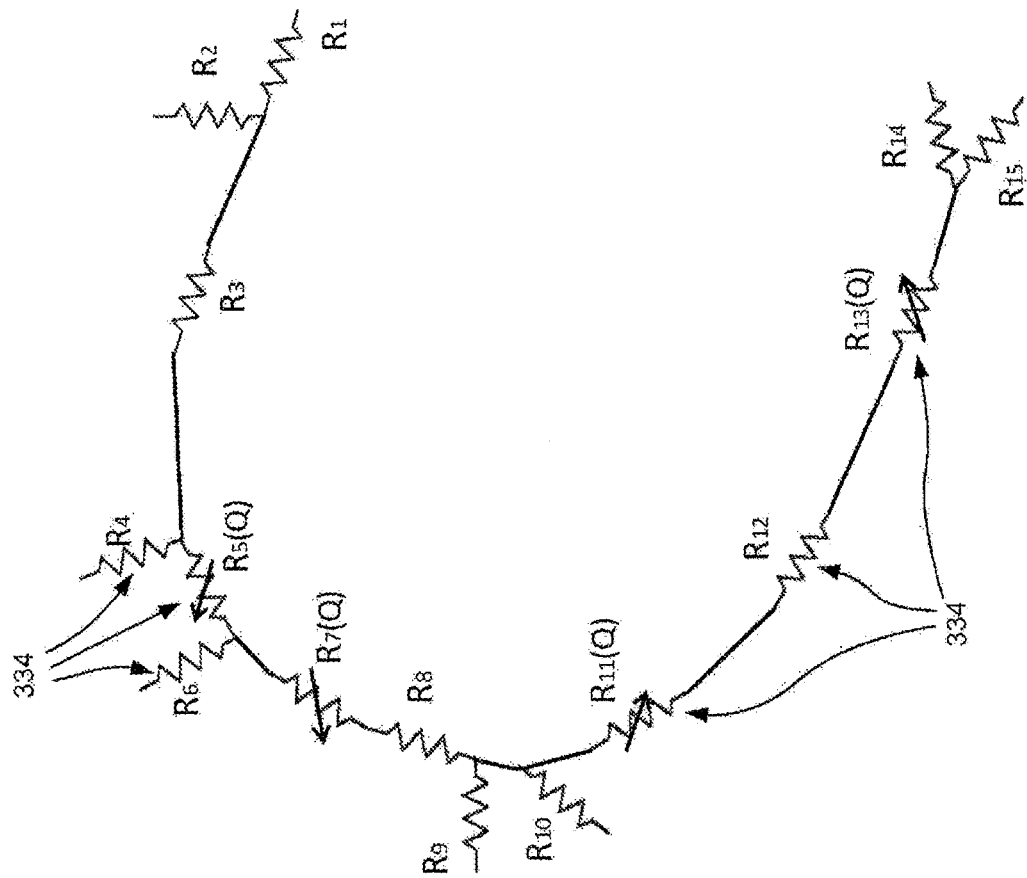
FIG. 15 shows the segments of FIG. 14 replaced by resistors, provided for forming a lumped parameter model.

The segments 332 may be approximated by a circuit diagram including one or more (linear or nonlinear) resistors 334 and/or other circuit elements (e.g., capacitors, inductors, etc.). FIG. 15 shows an example of the segments 332 replaced by a series of linear and nonlinear resistors 334. The individual resistances of the resistors 334 may be determined, e.g., based on an estimated flow and/or pressure across the corresponding segment 332.

The resistance may be constant, linear, or non-linear, e.g., depending on the estimated flow rate through the corresponding segment 332. For more complex geometries, such as a stenosis, the resistance may vary with flow rate. Resistances for various geometries may be determined based on a computational analysis (e.g., a finite difference, finite volume, spectral, lattice Boltzmann, particle-based, level set, isogeometric, or finite element method, or other computational fluid dynamics (CFD) analytical technique), and multiple solutions from the computational analysis performed under different flow and pressure conditions may be used to derive patient-specific, vessel-specific, and/or lesion-specific resistances. The results may be used to determine resistances for various types of features and geometries of any segment that may be modeled. As a result, deriving patient-specific, vessel-specific, and/or lesion-specific resistances as described above may allow the computer system to recognize and evaluate more complex geometry such as asymmetric stenosis, multiple lesions, lesions at bifurcations and branches and tortuous vessels, etc.

Capacitors may be also included, and capacitance may be determined, e.g., based on elasticity of the vessel walls of the corresponding segment. Inductors may be included, and inductance may be determined, e.g., based on inertial effects related to acceleration or deceleration of the blood volume flowing through the corresponding segment.

The individual values for resistance, capacitance, inductance, and other variables associated with other electrical components used in the lumped parameter model may be derived based on data from many patients, and similar vessel geometries may have similar values. Thus, empirical models may be developed from a large population of patient-specific data, creating a library of values corresponding to specific geometric features that may be applied to similar patients in future analyses. Geometries may be matched between two different vessel segments to automatically select the values for a segment 332 of a patient from a previous simulation.

ii. Exemplary Lumped Parameter Models

Figure 16:
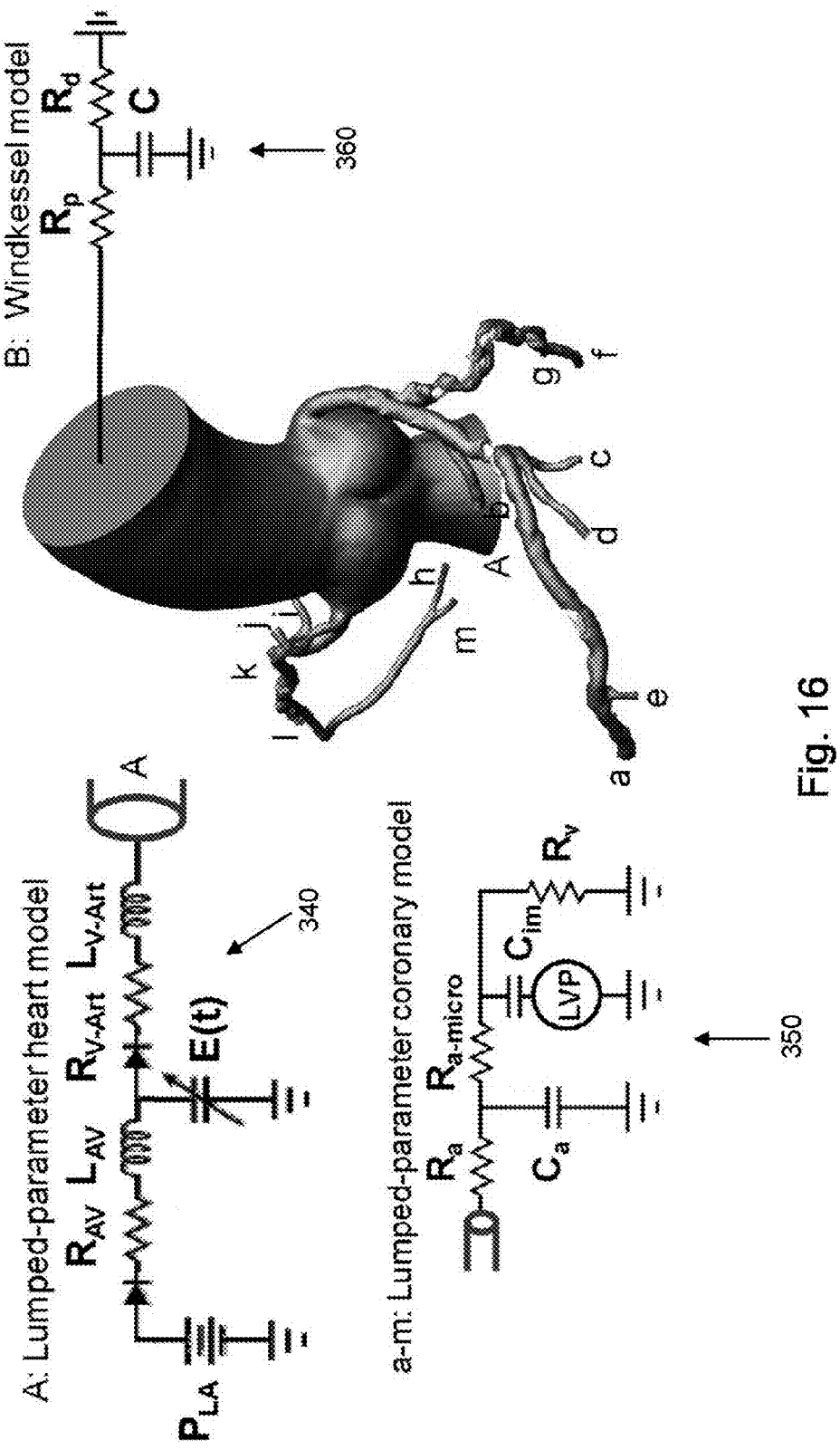
FIG. 16 shows exemplary lumped parameter models representing the upstream and downstream structures at the inflow and outflow boundaries of a solid model, according to an exemplary embodiment.

Alternatively, instead of performing the steps described above in connection with FIGS. 12-15, the lumped parameter models may be preset. For example, FIG. 16 shows examples of lumped parameter models 340, 350, 360 representing the upstream and downstream structures at the inflow and outflow boundaries 322, 324 of the solid model 320. End A is located at the inflow boundary 322, and ends a-m and B are located at the outflow boundaries.

A lumped parameter heart model 340 may be used to determine the boundary condition at the end A at the inflow boundary 322 of the solid model 320. The lumped parameter heart model 340 may be used to represent blood flow from the heart under hyperemia conditions. The lumped parameter heart model 340 includes various parameters (e.g., $P_{LA}$, $R_{AV}$, $L_{AV}$, $R_{V-Art}$, $L_{V-Art}$, and $E(t)$) that may be determined based on known information regarding the patient, e.g., an aortic pressure, the patient's systolic and diastolic blood pressures (e.g., as determined in step 100), the patient's cardiac output (the volume of blood flow from the heart, e.g., calculated based on the patient's stroke volume and heart rate determined in step 100), and/or constants determined experimentally.

A lumped parameter coronary model 350 may be used to determine the boundary conditions at the ends a-m at the outflow boundaries 324 of the solid model 320 located at the downstream ends of the main coronary arteries and/or the branches that extend therefrom. The lumped parameter coronary model 350 may be used to represent blood flow exiting from the modeled vessels through the ends a-m under hyperemia conditions. The lumped parameter coronary model 350 includes various parameters (e.g., $R_a$, $C_a$, $R_{a\text{-}micro}$, $C_{im}$, and $R_V$) that may be determined based on known information regarding the patient, e.g., the calculated myocardial mass (e.g., as determined in step 240) and terminal impedance at the ends a-m (e.g., determined based on the cross-sectional areas of the vessels at the ends a-m as determined in step 304).

For example, the calculated myocardial mass may be used to estimate a baseline (resting) mean coronary flow through the plurality of outflow boundaries 324. This relationship may be based on an experimentally-derived physiological law (e.g., of the physiological laws 20 of FIG. 1) that correlates the mean coronary flow Q with the myocardial mass M (e.g., as determined in step 240) as $Q \propto Q_0 M^\alpha$, where $\alpha$ is a preset scaling exponent and $Q_0$ is a preset constant. The total coronary flow Q at the outflow boundaries 324 under baseline (resting) conditions and the patient's blood pressure (e.g., as determined in step 100) may then be used to determine a total resistance R at the outflow boundaries 324 based on a preset, experimentally-derived equation.

The total resistance R may be distributed among the ends a-m based on the respective cross-sectional areas of the ends a-m (e.g., as determined in step 304). This relationship may be based on an experimentally-derived physiological law (e.g., of the physiological laws 20 of FIG. 1) that correlates the respective resistance at the ends a-m as $R_i \propto R_{i,0} d_i^\beta$ where $R_i$ is the resistance to flow at the i-th outlet, and $R_{i,0}$ is a preset constant, $d_i$ is the diameter of that outlet, and $\beta$ is a preset power law exponent, e.g., between −3 and −2, −2.7 for coronary flow, −2.9 for cerebral flow, etc. The coronary flow through the individual ends a-m and the mean pressures at the individual ends a-m (e.g., determined based on the individual cross-sectional areas of the ends a-m of the vessels as determined in step 304) may be used to determine a sum of the resistances of the lumped parameter coronary model 350 at the corresponding ends a-m (e.g., $R_a + R_{a\text{-}micro}$ $R_V$). Other parameters (e.g., $R_a/R_{a\text{-}micro}$, $C_a$, $C_{im}$) may be constants determined experimentally.

A Windkessel model 360 may be used to determine the boundary condition at the end B at the outflow boundary 324 of the solid model 320 located at the downstream end of the aorta toward the aortic arch. The Windkessel model 360 may be used to represent blood flow exiting from the modeled aorta through the end B under hyperemia conditions. The Windkessel model 360 includes various parameters (e.g., $R_p$, $R_d$, and C) that may be determined based on known information regarding the patient, e.g., the patient's cardiac output described above in connection with the lumped parameter heart model 340, the baseline mean coronary flow described above in connection with the lumped parameter coronary model 350, an aortic pressure (e.g., determined based on the cross-sectional area of the aorta at the end B as determined in step 304), and/or constants determined experimentally.

The boundary conditions, e.g., the lumped parameter models 340, 350, 360 (or any of the constants included therein) or other reduced order model, may be adjusted based on other factors. For example, resistance values may be adjusted (e.g., increased) if a patient has a lower flow to vessel size ratio due to a comparatively diminished capacity to dilate vessels under physiologic stress. Resistance values may also be adjusted if the patient has diabetes, is under medication, has undergone past cardiac events, etc.

Alternate lumped parameter or distributed, one-dimensional network models may be used to represent the coronary vessels downstream of the solid model 320. Myocardial perfusion imaging using MRI, CT, PET, or SPECT may be used to assign parameters for such models. Also, alternate imaging sources, e.g., magnetic resonance angiography (MRA), retrospective cine gating or prospective cine gating computed tomography angiography (CTA), etc., may be used to assign parameters for such models. Retrospective cine gating may be combined with image processing methods to obtain ventricular chamber volume changes over the cardiac cycle to assign parameters to a lumped parameter heart model.

Simplifying a portion of the patient's anatomy using the lumped parameter models 340, 350, 360, or other reduced order one- or two-dimensional model allows the computational analysis (e.g., step 402 of FIG. 3 described below) to be performed more quickly, particularly if the computational analysis is performed multiple times such as when evaluating possible treatment options (e.g., step 500 of FIG. 2) in addition to the untreated state (e.g., step 400 of FIGS. 2 and 3), while maintaining high accuracy with the final results.

In an exemplary embodiment, the determination of the boundary conditions may be performed by the computer system based on the user's inputs, such as patient-specific physiological data obtained in step 100.

C. Creating the Three-Dimensional Mesh

Referring back to FIG. 3, a three-dimensional mesh may be generated based on the solid model 320 generated in step 306 (step 312). FIGS. 17-19 show an example of a three-dimensional mesh 380 prepared based on the solid model 320 generated in step 306. The mesh 380 includes a plurality of nodes 382 (meshpoints or gridpoints) along the surfaces of the solid model 320 and throughout the interior of the solid model 320. The mesh 380 may be created with tetrahedral elements (having points that form the nodes 382), as shown in FIGS. 18 and 19. Alternatively, elements having other shapes may be used, e.g., hexahedrons or other polyhedrons, curvilinear elements, etc. In an exemplary embodiment, the number of nodes 382 may be in the millions, e.g., five to fifty million. The number of nodes 382 increases as the mesh 380 becomes finer. With a higher number of nodes 382, information may be provided at more points within the model 320, but the computational analysis may take longer to run since a greater number of nodes 382 increases the number of equations (e.g., the equations 30 shown in FIG. 1) to be solved. In an exemplary embodiment, the generation of the mesh 380 may be performed by the computer system, with or without a user's input (e.g., specifying a number of the nodes 382, the shapes of the elements, etc.).

Referring back to FIG. 3, the mesh 380 and the determined boundary conditions may be verified (step 314). The verification may be performed by a user and/or by the computer system. For example, the user and/or computer system may be able to identify certain errors with the mesh 380 and/or the boundary conditions that require the mesh 380 and/or the boundary conditions to be redone, e.g., if the mesh 380 is distorted or does not have sufficient spatial resolution, if the boundary conditions are not sufficient to perform the computational analysis, if the resistances determined in step 310 appear to be incorrect, etc. If so, then the mesh 380 and/or the boundary conditions may be determined to be unacceptable, and one or more of steps 304-314 may be repeated. If the mesh 380 and/or the boundary conditions are determined to be acceptable, then the method may proceed to step 402 described below.

In addition, the user may check that the obtained patient-specific information, or other measured parameters, such as cardiac output, blood pressures, height, weight, the myocardial mass calculated in step 240, are entered correctly and/or calculated correctly.

Accordingly, steps 304-314 shown in FIG. 3 and described above may be considered as substeps of step 300 of FIG. 2.

V. Performing the Computational Analysis and Outputting Results

As described above in connection with step 400 shown in FIG. 2, the exemplary method may include performing the computational analysis and outputting results. In an exemplary embodiment, step 400 may include the following steps.

A. Performing the Computational Analysis

Referring to FIG. 3, the computational analysis may be performed by the computer system (step 402). In an exemplary embodiment, step 402 may last minutes to hours, depending, e.g., on the number of nodes 382 in the mesh 380 (FIGS. 17-19), etc.

The analysis involves generating a series of equations that describe the blood flow in the model 320 from which the mesh 380 was generated. As described above, in the exemplary embodiment, the desired information relates to the simulation of blood flow through the model 320 under hyperemic conditions.

The analysis also involves using a numerical method to solve the three-dimensional equations of blood flow using the computer system. For example, the numerical method may be a known method, such as finite difference, finite volume, spectral, lattice Boltzmann, particle-based, level set, isogeometric, or finite element methods, or other computational fluid dynamics (CFD) numerical techniques.

Using these numerical methods, the blood may be modeled as a Newtonian, a non-Newtonian, or a multiphase fluid. The patient's hematocrit or other factors measured in step 100 may be used to determine blood viscosity for incorporation in the analysis. The blood vessel walls may be assumed to be rigid or compliant. In the latter case, equations for wall dynamics, e.g., the elastodynamics equations, may be solved together with the equations for blood flow. Time-varying three-dimensional imaging data obtained in step 100 may be used as an input to model changes in vessel shape over the cardiac cycle. An exemplary set of equations and steps for performing the computational analysis are disclosed in further detail, for example, in U.S. Pat. No. 6,236,878, which is entitled "Method for Predictive Modeling for Planning Medical Interventions and Simulating Physiological Conditions," and U.S. Patent Application Publication No. 2010/0241404 and U.S. Provisional Application No. 61/210,401, which are both entitled "Patient-Specific Hemodynamics of the Cardiovascular System," all of which are hereby incorporated by reference in their entirety.

The computational analysis using the prepared model and boundary conditions may determine blood flow and pressure at each of the nodes 382 of the mesh 380 representing the three-dimensional solid model 320. For example, the results of the computational analysis may include values for various parameters at each of the nodes 382, such as, but not limited to, various blood flow characteristics or parameters, such as blood flow velocity, pressure, flow rate, or computed parameters, such as cFFR, as described below. The parameters may also be interpolated across the three-dimensional solid model 320. As a result, the results of the computational analysis may provide the user with information that typically may be determined invasively.

Referring back to FIG. 3, the results of the computational analysis may be verified (step 404). The verification may be performed by a user and/or by the computer system. For example, the user and/or computer system may be able to identify certain errors with the results that require the mesh 380 and/or the boundary conditions to be redone or revised, e.g., if there is insufficient information due to an insufficient number of nodes 382, if the analysis is taking too long due to an excessive number of nodes 382, etc.

If the results of the computational analysis are determined to be unacceptable in step 404, then the user and/or computer system may determine, for example, whether and how to revise or refine the solid model 320 generated in step 306 and/or the mesh 380 generated in step 312, whether and how to revise the boundary conditions determined in step 310, or whether to make other revisions to any of the inputs for the computational analysis. Then, one or more steps described above, e.g., steps 306-314, 402, and 404 may be repeated based on the determined revisions or refinements.

B. Displaying Results for Blood Pressure, Flow, and cFFR

Referring back to FIG. 3, if the results of the computational analysis are determined to be acceptable in step 404, then the computer system may output certain results of the computational analysis. For example, the computer system may display images generated based on the results of the computational analysis, such as the images described above in connection with FIG. 1, such as the simulated blood pressure model 50, the simulated blood flow model 52, and/or the cFFR model 54. As noted above, these images indicate the simulated blood pressure, blood flow, and cFFR under simulated hyperemia conditions, e.g., since the boundary conditions determined in step 310 were determined with respect to hyperemia conditions.

The simulated blood pressure model 50 (FIG. 1) shows the local blood pressure (e.g., in millimeters of mercury or mmHg) throughout the patient's anatomy represented by the mesh 380 of FIGS. 17-19 under simulated hyperemia conditions. The computational analysis may determine the local blood pressure at each node 382 of the mesh 380, and the simulated blood pressure model 50 may assign a corresponding color, shade, or other visual indicator to the respective pressures such that the simulated blood pressure model 50 may visually indicate the variations in pressure throughout the model 50 without having to specify the individual values for each node 382. For example, the simulated blood pressure model 50 shown in FIG. 1 shows that, for this particular patient, under simulated hyperemia conditions, the pressure may be generally uniform and higher in the aorta (as indicated by the darker shading), and that the pressure gradually and continuously decreases as the blood flows downstream into the main coronary arteries and into the branches (as shown by the gradual and continuous lightening in shading toward the downstream ends of the branches). The simulated blood pressure model 50 may be accompanied by a scale indicating the specific numerical values for blood pressure, as shown in FIG. 1.

In an exemplary embodiment, the simulated blood pressure model 50 may be provided in color, and a color spectrum may be used to indicate variations in pressure throughout the model 50. The color spectrum may include red, orange, yellow, green, blue, indigo, and violet, in order from highest pressure to lowest pressure. For example, the upper limit (red) may indicate approximately 110 mmHg or more (or 80 mmHg, 90 mmHg, 100 mmHg, etc.), and the lower limit (violet) may indicate approximately 50 mmHg or less (or 20 mmHg, 30 mmHg, 40 mmHg, etc.), with green indicating approximately 80 mmHg (or other value approximately halfway between the upper and lower limits). Thus, the simulated blood pressure model 50 for some patients may show a majority or all of the aorta as red or other color towards the higher end of the spectrum, and the colors may change gradually through the spectrum (e.g., towards the lower end of the spectrum (down to violet)) towards the distal ends of the coronary arteries and the branches that extend therefrom. The distal ends of the coronary arteries for a particular patient may have different colors, e.g., anywhere from red to violet, depending on the local blood pressures determined for the respective distal ends.

The simulated blood flow model 52 (FIG. 1) shows the local blood velocity (e.g., in centimeters per second or cm/s) throughout the patient's anatomy represented by the mesh 380 of FIGS. 17-19 under simulated hyperemia conditions. The computational analysis may determine the local blood velocity at each node 382 of the mesh 380, and the simulated blood flow model 52 may assign a corresponding color, shade, or other visual indicator to the respective velocities such that the simulated blood flow model 52 may visually indicate the variations in velocity throughout the model 52 without having to specify the individual values for each node 382. For example, the simulated blood flow model 52 shown in FIG. 1 shows that, for this particular patient, under simulated hyperemia conditions, the velocity is generally higher in certain areas of the main coronary arteries and the branches (as indicated by the darker shading in area 53 in FIG. 1). The simulated blood flow model 52 may be accompanied by a scale indicating the specific numerical values for blood velocity, as shown in FIG. 1.

In an exemplary embodiment, the simulated blood flow model 52 may be provided in color, and a color spectrum may be used to indicate variations in velocity throughout the model 52. The color spectrum may include red, orange, yellow, green, blue, indigo, and violet, in order from highest velocity to lowest velocity. For example, the upper limit (red) may indicate approximately 100 (or 150) cm/s or more, and the lower limit (violet) may indicate approximately 0 cm/s, with green indicating approximately 50 cm/s (or other value approximately halfway between the upper and lower limits). Thus, the simulated blood flow model 52 for some patients may show a majority or all of the aorta as a mixture of colors towards the lower end of the spectrum (e.g., green through violet), and the colors may change gradually through the spectrum (e.g., towards the higher end of the spectrum (up to red)) at certain locations where the determined blood velocities increase.

The cFFR model 54 (FIG. 1) shows the local cFFR throughout the patient's anatomy represented by the mesh 380 of FIGS. 17-19 under simulated hyperemia conditions. As noted above, cFFR may be calculated as the ratio of the local blood pressure determined by the computational analysis (e.g., shown in the simulated blood pressure model 50) at a particular node 382 divided by the blood pressure in the aorta, e.g., at the inflow boundary 322 (FIG. 8). The computational analysis may determine the cFFR at each node 382 of the mesh 380, and the cFFR model 54 may assign a corresponding color, shade, or other visual indicator to the respective cFFR values such that the cFFR model 54 may visually indicate the variations in cFFR throughout the model 54 without having to specify the individual values for each node 382. For example, the cFFR model 54 shown in FIG. 1 shows that, for this particular patient, under simulated hyperemia conditions, cFFR may be generally uniform and approximately 1.0 in the aorta, and that cFFR gradually and continuously decreases as the blood flows downstream into the main coronary arteries and into the branches. The cFFR model 54 may also indicate cFFR values at certain points throughout the cFFR model 54, as shown in FIG. 1. The cFFR model 54 may be accompanied by a scale indicating the specific numerical values for cFFR, as shown in FIG. 1.

In an exemplary embodiment, the cFFR model 54 may be provided in color, and a color spectrum may be used to indicate variations in pressure throughout the model 54. The color spectrum may include red, orange, yellow, green, blue, indigo, and violet, in order from lowest cFFR (indicating functionally significant lesions) to highest cFFR. For example, the upper limit (violet) may indicate a cFFR of 1.0, and the lower limit (red) may indicate approximately 0.7 (or 0.75 or 0.8) or less, with green indicating approximately 0.85 (or other value approximately halfway between the upper and lower limits). For example, the lower limit may be determined based on a lower limit (e.g., 0.7, 0.75, or 0.8) used for determining whether the cFFR measurement indicates a functionally significant lesion or other feature that may require intervention. Thus, the cFFR model 54 for some patients may show a majority or all of the aorta as violet or other color towards the higher end of the spectrum, and the colors may change gradually through the spectrum (e.g., towards the higher end of the spectrum (up to anywhere from red to violet) towards the distal ends of the coronary arteries and the branches that extend therefrom. The distal ends of the coronary arteries for a particular patient may have different colors, e.g., anywhere from red to violet, depending on the local values of cFFR determined for the respective distal ends.

After determining that the cFFR has dropped below the lower limit used for determining the presence of a functionally significant lesion or other feature that may require intervention, the artery or branch may be assessed to locate the functionally significant lesion(s). The computer system or the user may locate the functionally significant lesion(s) based on the geometry of the artery or branch (e.g., using the cFFR model 54). For example, the functionally significant lesion(s) may be located by finding a narrowing or stenosis located near (e.g., upstream) from the location of the cFFR model 54 having the local minimum cFFR value. The computer system may indicate or display to the user the portion(s) of the cFFR model 54 (or other model) that includes the functionally significant lesion(s).

Figure 20:
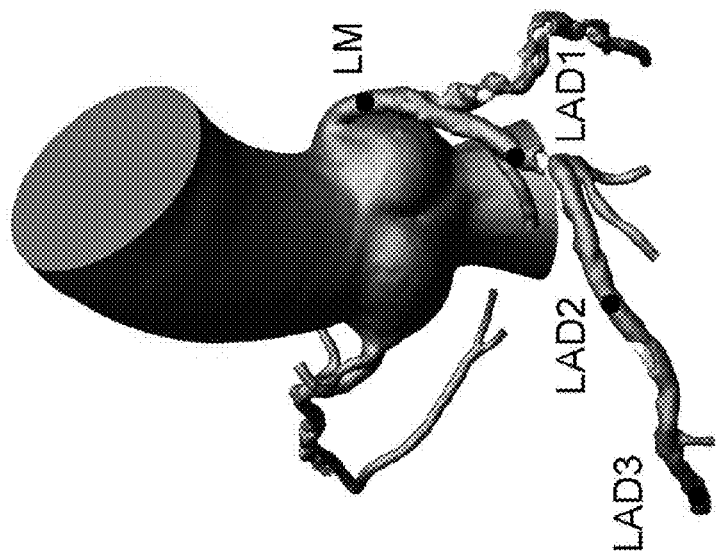
FIG. 20 shows a model of the patient's anatomy including blood flow information with certain points on the model identified by individual reference labels.
Figure 21:
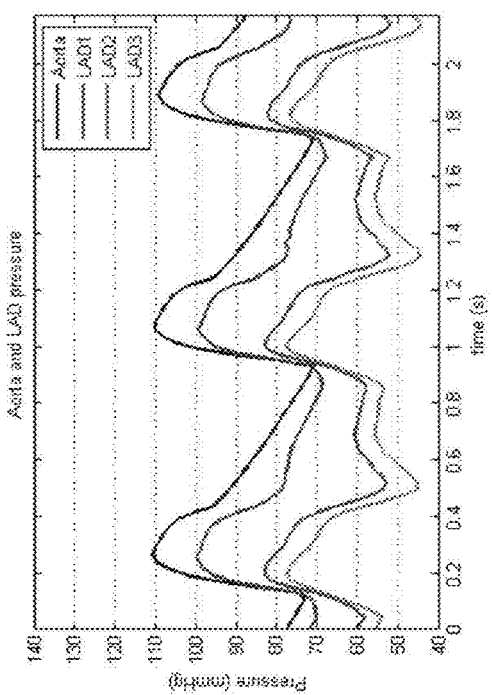
FIG. 21 is a graph of simulated blood pressure over time in the aorta and at some of the points identified in FIG. 20.
Figure 22:
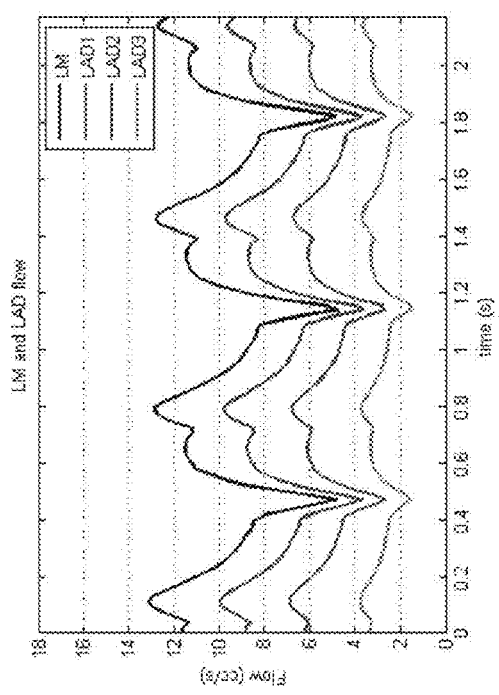
FIG. 22 is a graph of simulated blood flow over time at each of the points identified in FIG. 20.

Other images may also be generated based on the results of the computational analysis. For example, the computer system may provide additional information regarding particular main coronary arteries, e.g., as shown in FIGS. 20-22. The coronary artery may be chosen by the computer system, for example, if the particular coronary artery includes the lowest cFFR. Alternatively, the user may select the particular coronary artery.

FIG. 20 shows a model of the patient's anatomy including results of the computational analysis with certain points on the model identified by individual reference labels (e.g., LM, LAD1, LAD2, LAD3, etc.). In the exemplary embodiment shown in FIG. 21, the points are provided in the LAD artery, which is the main coronary artery having the lowest cFFR for this particular patient, under simulated hyperemia conditions.

FIGS. 21 and 22 show graphs of certain variables over time at some or all of these points (e.g., LM, LAD1, LAD2, LAD3, etc.) and/or at certain other locations on the model (e.g., in the aorta, etc.). FIG. 21 is a graph of the pressure (e.g., in millimeters of mercury or mmHg) over time in the aorta and at points LAD1, LAD2, and LAD3 indicated in FIG. 20. The top plot on the graph indicates the pressure in the aorta, the second plot from the top indicates the pressure at point LAD1, the third plot from the top indicates the pressure at point LAD2, and the bottom plot indicates the pressure at point LAD3. FIG. 22 is a graph of the flow (e.g., in cubic centimeters per second or cc/s) over time at points LM, LAD1, LAD2, and LAD3 indicated in FIG. 20. In addition, other graphs may be provided, such as a graph of shear stress over time at some or all of these points and/or at other points. The top plot on the graph indicates the flow at point LM, the second plot from the top indicates the flow at point LAD1, the third plot from the top indicates the flow at point LAD2, and the bottom plot indicates the flow at point LAD3. Graphs may also be provided that show the change in these variables, e.g., blood pressure, flow, velocity, or cFFR, along the length of a particular main coronary artery and/or the branches extending therefrom.

Optionally, the various graphs and other results described above may be finalized in a report (step 406). For example, the images and other information described above may be inserted into a document having a set template. The template may be preset and generic for multiple patients, and may be used for reporting the results of computational analyses to physicians and/or patients. The document or report may be automatically completed by the computer system after the computational analysis is completed.

Figure 23:
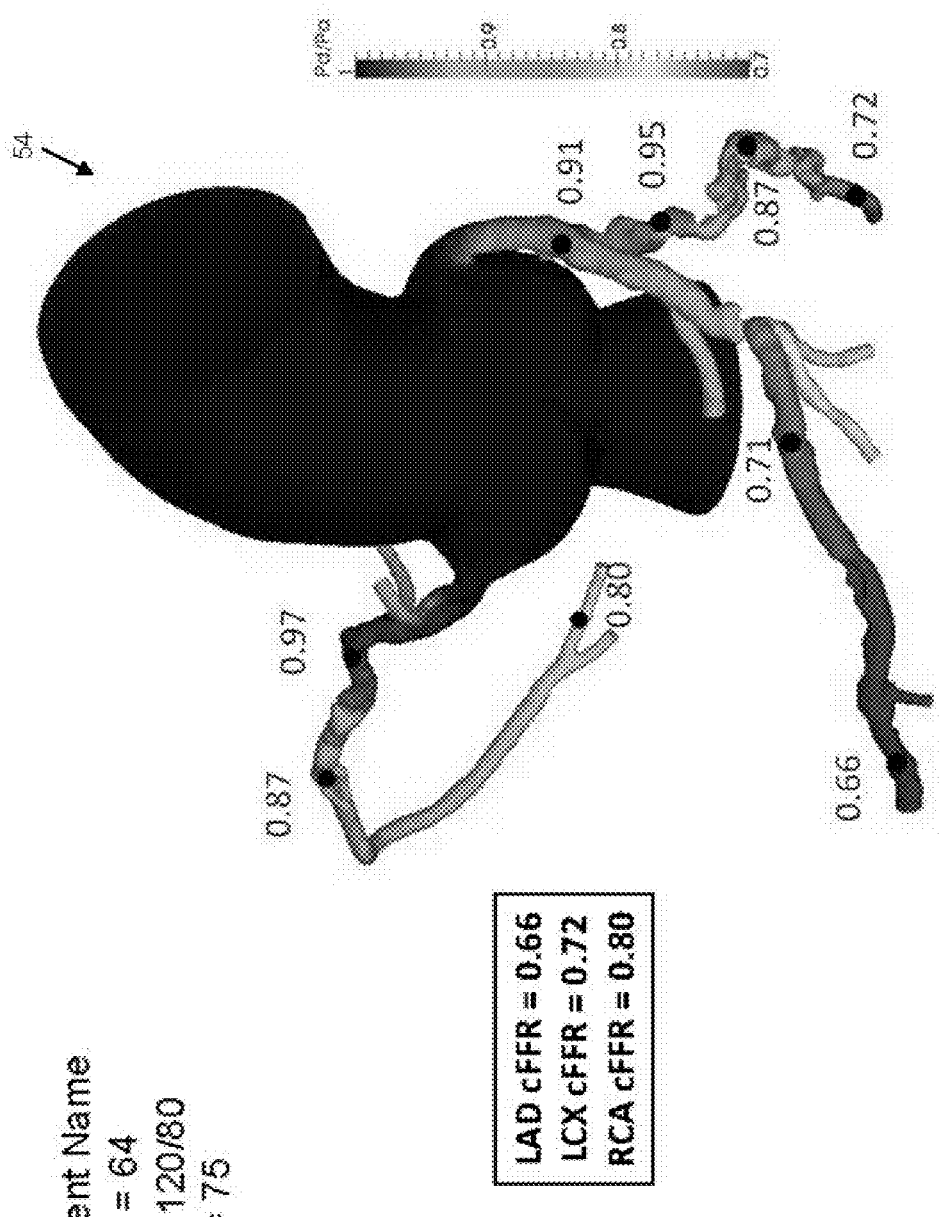
FIG. 23 is a finalized report, according to an exemplary embodiment.
Figure 24:
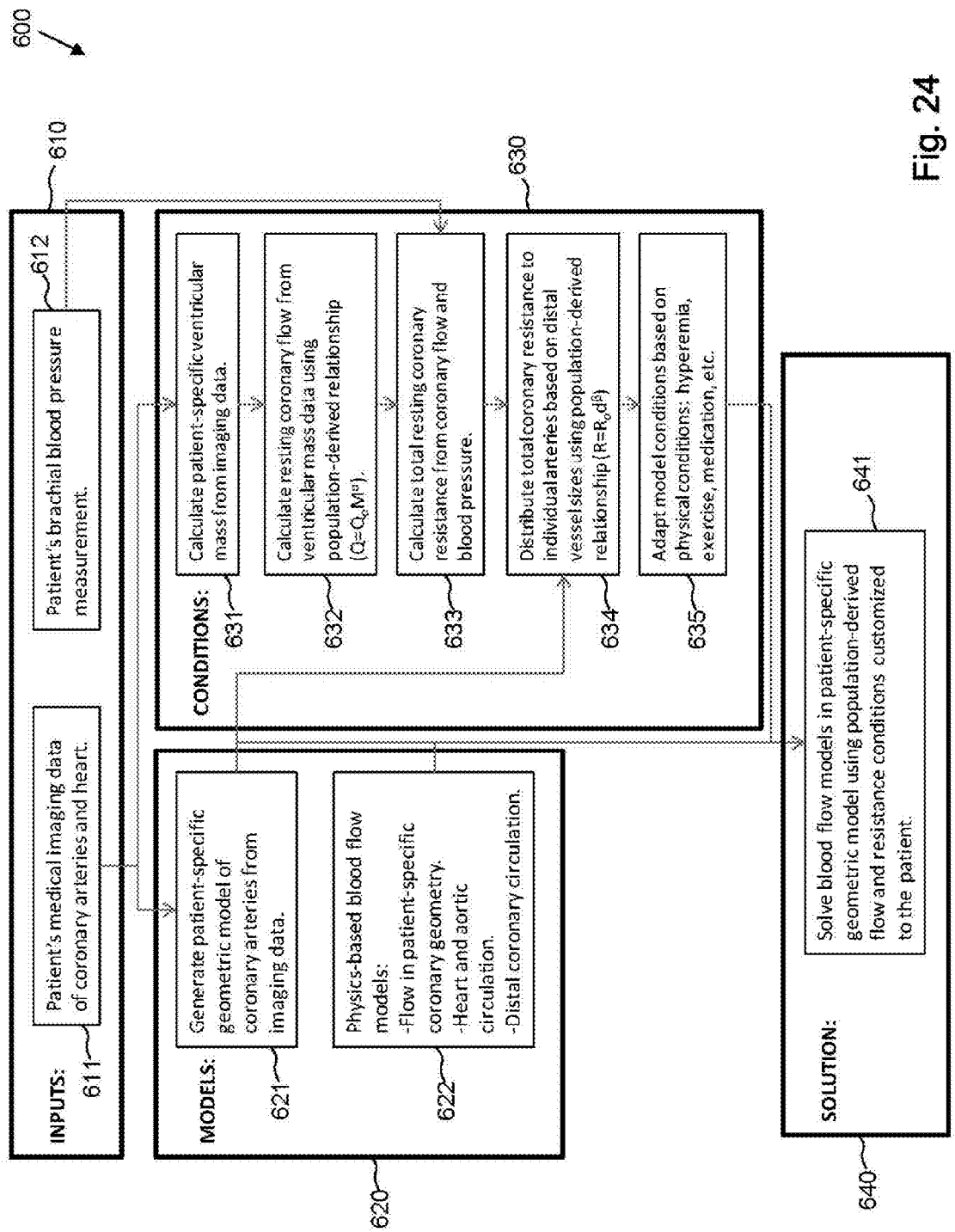
FIG. 24 is a flow chart of a method for providing various information relating to coronary blood flow in a specific patient, according to an exemplary embodiment.

For example, the finalized report may include the information shown in FIG. 23. FIG. 23 includes the cFFR model 54 of FIG. 1 and also includes summary information, such as the lowest cFFR values in each of the main coronary arteries and the branches that extend therefrom. For example, FIG. 23 indicates that the lowest cFFR value in the LAD artery is 0.66, the lowest cFFR value in the LCX artery is 0.72, the lowest cFFR value in the RCA artery is 0.80. Other summary information may include the patient's name, the patient's age, the patient's blood pressure (BP) (e.g., obtained in step 100), the patient's heart rate (HR) (e.g., obtained in step 100), etc. The finalized report may also include versions of the images and other information generated as described above that the physician or other user may access to determine further information. The images generated by the computer system may be formatted to allow the physician or other user to position a cursor over any point to determine the value of any of the variables described above, e.g., blood pressure, velocity, flow, cFFR, etc., at that point.

The finalized report may be transmitted to the physician and/or the patient. The finalized report may be transmitted using any known method of communication, e.g., a wireless or wired network, by mail, etc. Alternatively, the physician and/or patient may be notified that the finalized report is available for download or pick-up. Then, the physician and/or patient may log into the web-based service to download the finalized report via a secure communication line.

C. Verifying Results

Referring back to FIG. 3, the results of the computational analysis may be independently verified (step 408). For example, the user and/or computer system may be able to identify certain errors with the results of the computational analysis, e.g., the images and other information generated in step 406, that require any of the above described steps to be redone. If such errors are identified, then the results of the computational analysis may be determined to be unacceptable, and certain steps, e.g., steps 100, 200, 300, 400, substeps 102, 202-208, 240-260, 304-314, and 402-408, etc., may be repeated.

Accordingly, steps 402-408 shown in FIG. 3 and described above may be considered as substeps of step 400 of FIG. 2.

Another method for verifying the results of the computational analysis may include measuring any of the variables included in the results, e.g., blood pressure, velocity, flow, cFFR, etc., from the patient using another method. In an exemplary embodiment, the variables may be measured (e.g., invasively) and then compared to the results determined by the computational analysis. For example, FFR may be determined, e.g., using a pressure wire inserted into the patient as described above, at one or more points within the patient's anatomy represented by the solid model 320 and the mesh 380. The measured FFR at a location may be compared with the cFFR at the same location, and the comparison may be performed at multiple locations. Optionally, the computational analysis and/or boundary conditions may be adjusted based on the comparison.

VI. Providing Patient-Specific Treatment Planning

As described above in connection with step 500 shown in FIG. 2, the exemplary method may include providing patient-specific treatment planning. In an exemplary embodiment, step 500 may include the following steps. Although FIG. 3 does not show the following steps, it is understood that these steps may be performed in conjunction with the steps shown in FIG. 3, e.g., after steps 406 or 408. Moreover, as described above, any of the following described sub-steps of step 500 may be performed by a computing system, such as computer 40, and/or by one or more computing systems, servers systems, and/or web servers.

As described above, the cFFR model 54 shown in FIGS. 1 and 23 indicates the cFFR values throughout the patient's anatomy represented by the mesh 380 of FIGS. 17-19 in an untreated state and under simulated hyperemia conditions. Using this information, the physician may prescribe treatments to the patient, such as an increase in exercise, a change in diet, a prescription of medication, surgery on any portion of the modeled anatomy or other portions of the heart (e.g., coronary artery bypass grafting, insertion of one or more coronary stents, etc.), etc.

To determine which treatment(s) to prescribe, the computer system may be used to predict how the information determined from the computational analysis would change based on such treatment(s). For example, certain treatments, such as insertion of stent(s) or other surgeries, may result in a change in geometry of the modeled anatomy. Accordingly, in an exemplary embodiment, the solid model 320 generated in step 306 may be revised to indicate a widening of one or more lumens where a stent is inserted.

For example, the cFFR model 54 shown in FIGS. 1 and 23 indicates that the lowest cFFR value in the LAD artery is 0.66, the lowest cFFR value in the LCX artery is 0.72, the lowest cFFR value in the RCA artery is 0.80. Treatment may be proposed if a cFFR value is, for example, less than 0.75. Accordingly, the computer system may propose to the user revising the solid model 320 to indicate a widening of the LAD artery and the LCX artery to simulate inserting stents in these coronary arteries. The user may be prompted to choose the location and amount of widening (e.g., the length and diameter) corresponding to the location and size of the simulated stent. Alternatively, the location and amount of widening may be determined automatically by the computer system based on various factors, such as the location of the node(s) with cFFR values that are less than 0.75, a location of a significant narrowing of the vessels, sizes of conventional stents, etc.

Figure 25:
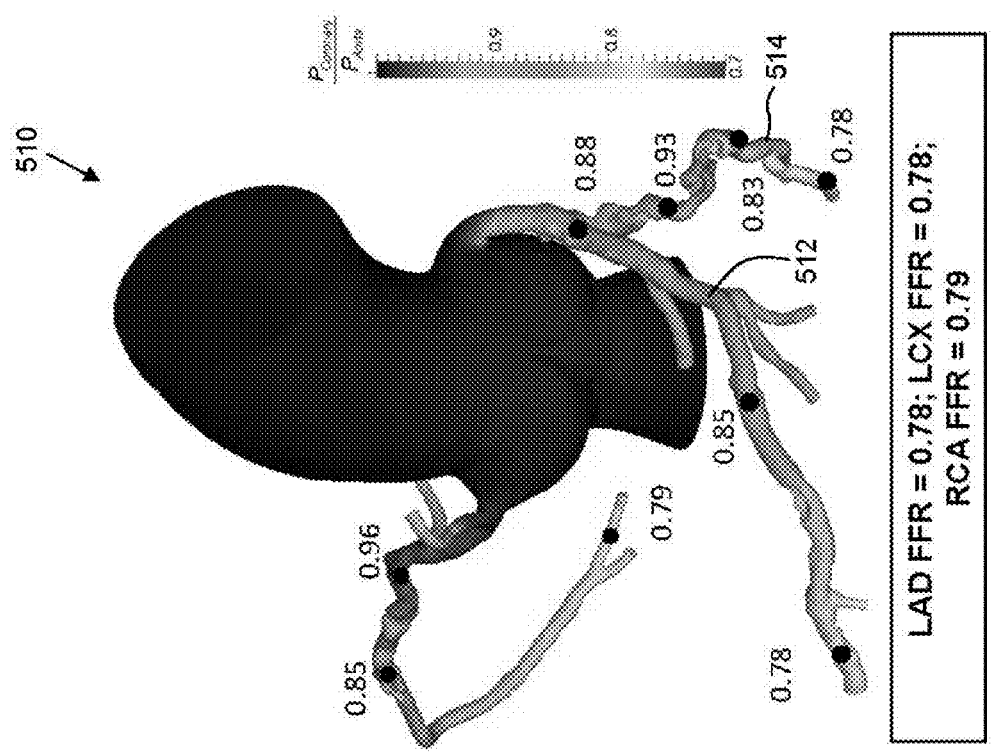
FIG. 25 shows a modified cFFR model determined based on a solid model created by widening a portion of the left anterior descending (LAD) artery and a portion of the LCX artery, according to an exemplary embodiment.

FIG. 25 shows an example of a modified cFFR model 510 determined based on a solid model created by widening a portion of the LAD artery at location 512 and a portion of the LCX artery at location 514. In an exemplary embodiment, any of the steps described above, e.g., steps 310-314 and 402-408, may be repeated using the modified solid model. In step 406, the finalized report may include the information relating to the untreated patient (e.g., without the stents), such as the information shown in FIG. 23, and information relating to the simulated treatment for the patient, such as the information shown in FIGS. 25 and 26.

FIG. 25 includes the modified cFFR model 510 and also includes summary information, such as the lowest cFFR values in the main coronary arteries and the branches that extend therefrom for the modified solid model associated with the proposed treatment. For example, FIG. 25 indicates that the lowest cFFR value in the LAD artery (and its downstream branches) is 0.78, the lowest cFFR value in the LCX artery (and its downstream branches) is 0.78, the lowest cFFR value in the RCA artery (and its downstream branches) is 0.79. Accordingly, a comparison of the cFFR model 54 of the untreated patient (without stents) and the cFFR model 510 for the proposed treatment (with stents inserted) indicates that the proposed treatment may increase the minimum cFFR in the LAD artery from 0.66 to 0.78 and would increase the minimum cFFR in the LCX artery from 0.72 to 0.76, while there would be a minimal decrease in the minimum cFFR in the RCA artery from 0.80 to 0.79.

Figure 26:
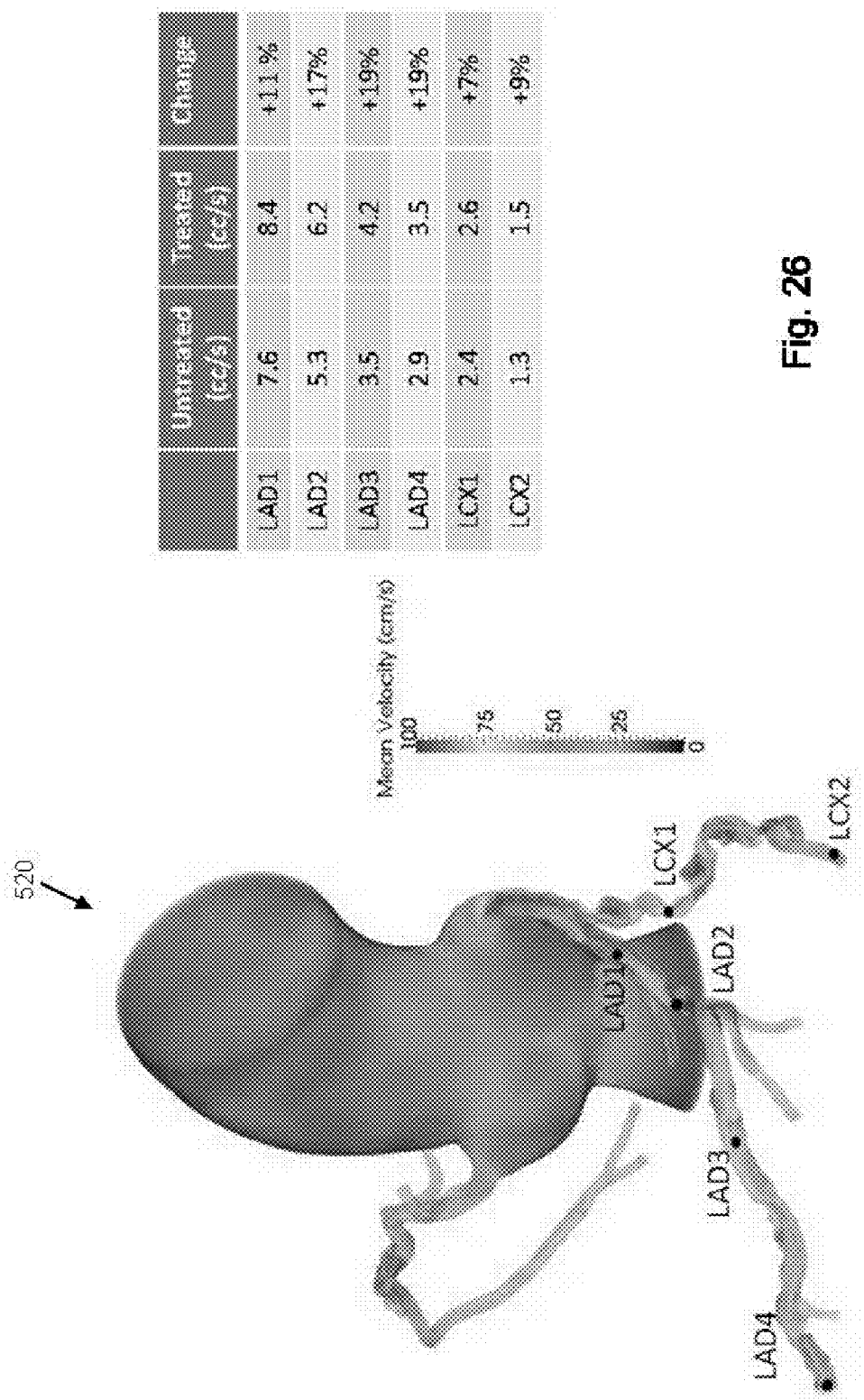
FIG. 26 shows an example of a modified simulated blood flow model after widening a portion of the LAD artery and a portion of the left circumflex (LCX) artery, according to an exemplary embodiment.

FIG. 26 shows an example of a modified simulated blood flow model 520 determined after widening portions of the LAD artery at location 512 and of the LCX artery at location 514 as described above. FIG. 26 also includes summary information, such as the blood flow values at various locations in the main coronary arteries and the branches that extend therefrom for the modified solid model associated with the proposed treatment. For example, FIG. 26 indicates blood flow values for four locations LAD1, LAD2, LAD3, and LAD4 in the LAD artery and for two locations LCX1 and LCX2 in the LCX artery for the untreated patient (without stents) and for the treated patient (with stents inserted). FIG. 26 also indicates a percentage change in blood flow values between the untreated and treated states. Accordingly, a comparison of the simulated blood flow model 52 of the untreated patient and the simulated blood flow model 520 for the proposed treatment indicates that the proposed treatment may increase the flow through the LAD artery and LCX artery at all of the locations LAD1-LAD4, LCX1, and LCX2 by 9% to 19%, depending on the location.

Other information may also be compared between the untreated and treated states, such as coronary artery blood pressure. Based on this information, the physician may discuss with the patient whether to proceed with the proposed treatment option.

Other treatment options may also involve modifying the solid model 320 in different ways. For example, coronary artery bypass grafting may involve creating new lumens or passageways in the solid model 320 and removing a lesion may also involve widening a lumen or passage. Other treatment options may not involve modifying the solid model 320. For example, an increase in exercise or exertion, a change in diet or other lifestyle change, a prescription of medication, etc., may involve changing the boundary conditions determined in step 310, e.g., due to vasoconstriction, dilation, decreased heart rate, etc. For example, the patient's heart rate, cardiac output, stroke volume, blood pressure, coronary microcirculation function, the configurations of the lumped parameter models, etc., may depend on the medication prescribed, the type and frequency of exercise adopted (or other exertion), the type of lifestyle change adopted (e.g., cessation of smoking, changes in diet, etc.), thereby affecting the boundary conditions determined in step 310 in different ways.

In an exemplary embodiment, modified boundary conditions may be determined experimentally using data from many patients, and similar treatment options may require modifying the boundary conditions in similar ways. Empirical models may be developed from a large population of patient-specific data, creating a library of boundary conditions or functions for calculating boundary conditions, corresponding to specific treatment options that may be applied to similar patients in future analyses.

After modifying the boundary conditions, the steps described above, e.g., steps 312, 314, and 402-408, may be repeated using the modified boundary conditions, and in step 406, the finalized report may include the information relating to the untreated patient, such as the information shown in FIG. 23, and information relating to the simulated treatment for the patient, such as the information shown in FIGS. 25 and 26.

Alternatively, the physician, the patient, or other user may be provided with a user interface that allows interaction with a three-dimensional model (e.g., the solid model 320 of FIG. 8). The model 320 may be divided into user-selectable segments that may be edited by the user to reflect one or more treatment options. For example, the user may select a segment with a stenosis (or occlusion, e.g., an acute occlusion) and adjust the segment to remove the stenosis, the user may add a segment to the model 320 to serve as a bypass, etc. The user may also be prompted to specify other treatment options and/or physiologic parameters that may alter the boundary conditions determined above, e.g., a change in a cardiac output, a heart rate, a stroke volume, a blood pressure, an exercise or exertion level, a hyperemia level, medications, etc. In an alternate embodiment, the computer system may determine or suggest a treatment option.

The user interface may allow interaction with the three-dimensional model 320 to allow the user to simulate a stenosis (or occlusion, e.g., an acute occlusion). For example, the user may select a segment for including the stenosis, and the computer system may be used to predict how the information determined from the computational analysis would change based on the addition of the stenosis. Thus, the methods described herein may be used to predict the effect of occluding an artery.

The user interface may also allow interaction with the three-dimensional model 320 to simulate a damaged artery or removal of an artery, which may occur, for example, in certain surgical procedures, such as when removing cancerous tumors. The model may also be modified to simulate the effect of preventing blood flow through certain arteries in order to predict the potential for collateral pathways for supplying adequate blood flow for the patient.

A. Using Reduced Order Models to Compare Different Treatment Options

Figure 27:
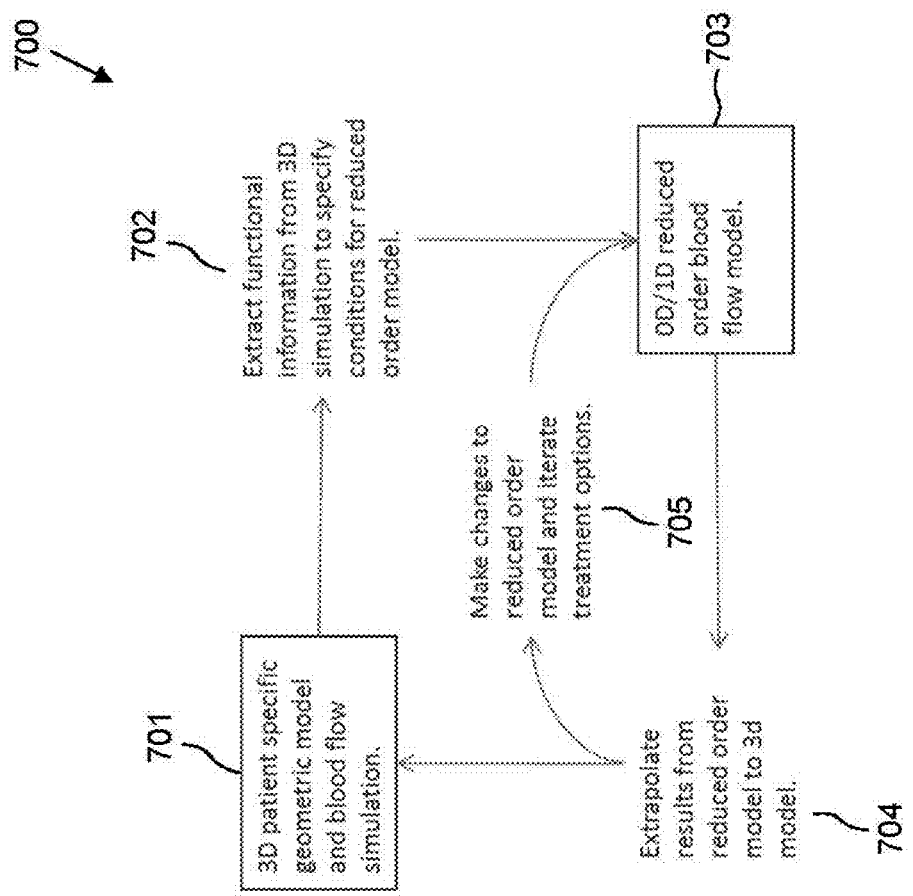
FIG. 27 is a flow chart of a method for simulating various treatment options using a reduced order model, according to an exemplary embodiment.

In an exemplary embodiment, the computer system may allow the user to simulate various treatment options more quickly by replacing the three-dimensional solid model 320 or mesh 380 with a reduced order model. FIG. 27 shows a schematic diagram relating to a method 700 for simulating various treatment options using a reduced order model, according to an exemplary embodiment. The method 700 may be implemented in the computer system described above.

One or more patient-specific simulated blood flow models representing blood flow or other parameters may be output from the computational analysis described above (step 701). For example, the simulated blood flow models may include the simulated blood pressure model 50 of FIG. 1, the simulated blood flow model 52 of FIG. 1, the cFFR model 54 of FIG. 1, etc., provided using the methods described above and shown in FIGS. 2 and 3. As described above, the simulated blood flow model may include a three-dimensional geometrical model of the patient's anatomy.

Functional information may be extracted from the simulated blood flow models in order to specify conditions for a reduced order model (step 702). For example, the functional information may include the blood pressure, flow, or velocity information determined using the computational analysis described above.

A reduced order (e.g., zero-dimensional or one-dimensional) model may be provided to replace the three-dimensional solid model 320 used to generate the patient specific simulated blood flow models generated in step 701, and the reduced order model may be used to determine information about the coronary blood flow in the patient (step 703). For example, the reduced order model may be a lumped parameter model generated as described above in connection with step 310 of FIG. 3. Thus, the lumped parameter model is a simplified model of the patient's anatomy that may be used to determine information about the coronary blood flow in the patient without having to solve the more complex system of equations associated with the mesh 380 of FIGS. 17-19.

Information determined from solving the reduced order model in step 703 may then be mapped or extrapolated to a three-dimensional solid model (e.g., the solid model 320) of the patient's anatomy (step 704), and the user may make changes to the reduced order model as desired to simulate various treatment options and/or changes to the physiologic parameters for the patient, which may be selected by the user (step 705). The selectable physiologic parameters may include cardiac output, exercise or exertion level, level of hyperemia, types of medications, etc. The selectable treatment options may include removing a stenosis, adding a bypass, etc.

Then, the reduced order model may be modified based on the treatment options and/or physiologic parameters selected by the user, and the modified reduced order model may be used to determine information about the coronary blood flow in the patient associated with the selected treatment option and/or physiologic parameter (step 703). Information determined from solving the reduced order model in step 703 may then be mapped or extrapolated to the three-dimensional solid model 320 of the patient's anatomy to predict the effects of the selected treatment option and/or physiologic parameter on the coronary blood flow in the patient's anatomy (step 704).

Steps 703-705 may be repeated for various different treatment options and/or physiologic parameters to compare the predicted effects of various treatment options to each other and to the information about the coronary blood flow in the untreated patient. As a result, predicted results for various treatment options and/or physiologic parameters may be evaluated against each other and against information about the untreated patient without having to rerun the more complex analysis using the three-dimensional mesh 380. Instead, a reduced order model may be used, which may allow the user to analyze and compare different treatment options and/or physiologic parameters more easily and quickly.

Figure 28:
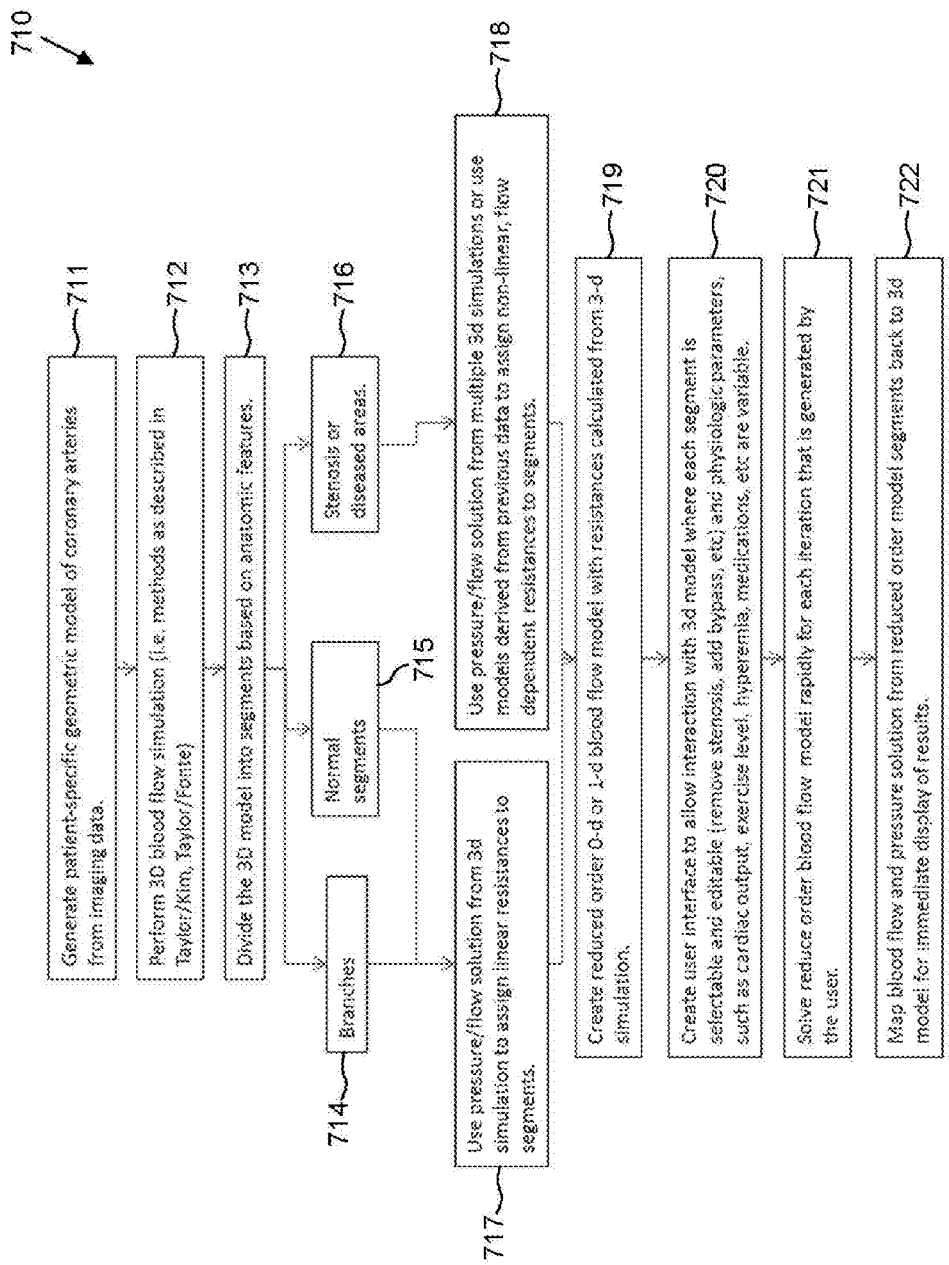
FIG. 28 is a flow chart of a method for simulating various treatment options using a reduced order model, according to another exemplary embodiment.

FIG. 28 shows further aspects of the exemplary method for simulating various treatment options using a reduced order model, according to an exemplary embodiment. The method 700 may be implemented in the computer system described above.

As described above in connection with step 306 of FIG. 3, a patient-specific geometric model may be generated based on imaging data for the patient (step 711). For example, the imaging data may include the CCTA data obtained in step 100 of FIG. 2, and the geometric model may be the solid model 320 of FIG. 8 generated in step 306 of FIG. 3, and/or the mesh 380 of FIGS. 17-19 generated in step 312 of FIG. 3.

Using the patient-specific three-dimensional geometric model, the computational analysis may be performed, e.g., as described above in connection with step 402 of FIG. 3, to determine information about the patient's coronary blood flow (step 712). The computational analysis may output one or more three-dimensional patient-specific simulated blood flow models representing blood flow or other parameters, e.g., the simulated blood pressure model 50 of FIG. 1, the simulated blood flow model 52 of FIG. 1, the cFFR model 54 of FIG. 1, etc.

The simulated blood flow model may be segmented (e.g., as described above in connection with FIG. 14) based on the anatomical features of the model (step 713). For example, branches extending from the main coronary arteries may be provided in separate segments (step 714), portions with stenosis or diseased areas may be provided in separate segments (step 716), and portions between the branches and the portions with stenosis or diseased areas may be provided in separate segments (step 715). Varying degrees of resolution may be provided in segmenting the simulated blood flow model such that each vessel may include a plurality of short, discrete segments or longer segments, e.g., including the entire vessel. Also, various techniques may be provided for segmenting the simulated blood flow model, including generating centerlines and sectioning based on the generated centerlines, or detecting branch points and sectioning based on the detected branch points. The diseased portions and stenoses may be identified, e.g., by measuring the cross-sectional area along the length of the centerline and calculating locally minimum cross-sectional areas. Steps 711-716 may be considered as substeps of step 701 of FIG. 27.

The segments may be replaced by components of a lumped parameter model, such as resistors, capacitors, inductors, etc., as described above in connection with FIG. 15. The individual values for the resistance, capacitance, inductance, and other variables associated with other electrical components used in the lumped parameter model may be derived from the simulated blood flow models provided in step 712. For example, for branches and portions between the branches and the portions with stenosis or diseased areas, information derived from the simulated blood flow model may be used to assign linear resistances to the corresponding segments (step 717). For portions with complex geometry, such as a stenosis or diseased area, resistance may vary with flow rate. Thus, multiple computational analyses may be used to obtain simulated blood flow models for various flow and pressure conditions to derive patient-specific, vessel-specific, and lesion-specific resistance functions for these complex geometries, as described above in connection with FIG. 15. Accordingly, for portions with stenosis or diseased areas, information derived from these multiple computational analyses or models derived from previous data may be used to assign non-linear, flow-dependent resistances to corresponding segments (step 718). Steps 717 and 718 may be considered as substeps of step 702 of FIG. 27.

Using the resistances determined in steps 717 and 718, a reduced order (e.g., zero-dimensional or one-dimensional) model may be generated (step 719). For example, the reduced order model may be a lumped parameter model generated as described above in connection with step 310 of FIG. 3. Thus, the lumped parameter model is a simplified model of the patient's anatomy that may be used to determine information about the coronary blood flow in the patient without having to solve the more complex system of equations associated with the mesh 380 of FIGS. 17-19.

A user interface may be provided that allows the user to interact with the reduced order model created in step 719 (step 720). For example, the user may select and edit different segments of the reduced order model to simulate different treatment options and/or may edit various physiologic parameters. For example, intervention, such as insertion of a stent to repair of a diseased region, may be modeled by decreasing the resistance of the segment where the stent is to be inserted. Forming a bypass may be modeled by adding a segment having a low resistance parallel to a diseased segment.

The modified reduced order model may be solved to determine information about the coronary blood flow in the patient under the treatment and/or change in physiologic parameters selected in step 720 (step 721). The solution values for flow and pressure in each segment determined in step 721 may then be compared to the three-dimensional solution determined in step 712, and any difference may be minimized by adjusting the resistance functions of the segments (e.g., as determined in steps 717 and 718) and resolving the reduced order model (e.g., step 721) until the solutions match. As a result, the reduced order model may be created and then solved with a simplified set of equations that allows for relatively rapid computation (e.g., compared to a full three-dimensional model) and may be used to solve for flow rate and pressure that may closely approximate the results of a full three-dimensional computational solution. The reduced order model allows for relatively rapid iterations to model various different treatment options.

Information determined from solving the reduced order model in step 721 may then be mapped or extrapolated to a three-dimensional solid model of the patient's anatomy (e.g., the solid model 320) (step 722). Steps 719-722 may be similar to steps 703-705 of FIG. 27 and may be repeated as desired by the user to simulate different combinations of treatment options and/or physiologic parameters.

Alternatively, rather than calculating the resistance along segments from the three-dimensional model (e.g., as described above for steps 717 and 718), flow and pressure at intervals along the centerline may be prescribed into a lumped parameter or one-dimensional model. The effective resistances or loss coefficients may be solved for under the constraints of the boundary conditions and prescribed flow and pressure.

Also, the flow rates and pressure gradients across individual segments may be used to compute an epicardial coronary resistance using the solution derived from the reduced-order model (e.g., as described above for step 721). The epicardial coronary resistance may be calculated as an equivalent resistance of the epicardial coronary arteries (the portions of the coronary arteries and the branches that extend therefrom included in the patient-specific model reconstructed from medical imaging data). This may have clinical significance in explaining why patients with diffuse atherosclerosis in the coronary arteries may exhibit symptoms of ischemia (restriction in blood supply). Also, the flow per unit of myocardial tissue volume (or mass) and/or the flow per unit of cardiac work under conditions of simulated pharmacologically-induced hyperemia or varying exercise intensity may be calculated using data from the reduced-order models.

B. Modifying Patient-Specific Geometrical Models to Optimize Treatment Options

In addition to previously-described techniques for enabling a user to revise geometry in solid model 320 to widen lumens, and enabling a user to modify a reduced order model based on various treatment options, other embodiments of systems and methods are now disclosed for automatically evaluating treatment options by modifying patient-specific geometric models. For example, as described above, a cardiologist may review a three-dimensional patient specific geometrical model, and decide to make changes to the model to reflect a treatment option that the cardiologist believes may provide better blood flow properties. In addition, a cardiologist may operate a computer system to update a reduced-order model based on the changes that the cardiologist makes to the geometrical model, to calculate whether the cardiologist's belief about improved blood flow properties is correct.

However, additional embodiments are now described for automatically evaluating treatment options by modifying patient-specific geometric models. For example, a computer system may automatically modify patient-specific geometric models and evaluate treatment options, even for treatment options that a cardiologist does not necessarily know will improve blood flow properties. Moreover, a computer may automatically modify patient-specific geometric models, hundreds or even thousands of times to reflect hundreds or even thousands of different possible treatment options. For example, the computer system may automatically model numerous different possible positions and types of bypass graft and/or stent interventions, model a patient's coronary geometry based on implementation of those numerous types of interventions, and then automatically identify one or more suitable or desirable interventions by automatically analyzing the models, e.g., using reduced order modeling. As will be described in more detail below, any type of computing system, such as computer 40 (FIG. 1), may be used to process and evaluate patient-specific imaging data according to the exemplary method of FIG. 29.

Figure 29:
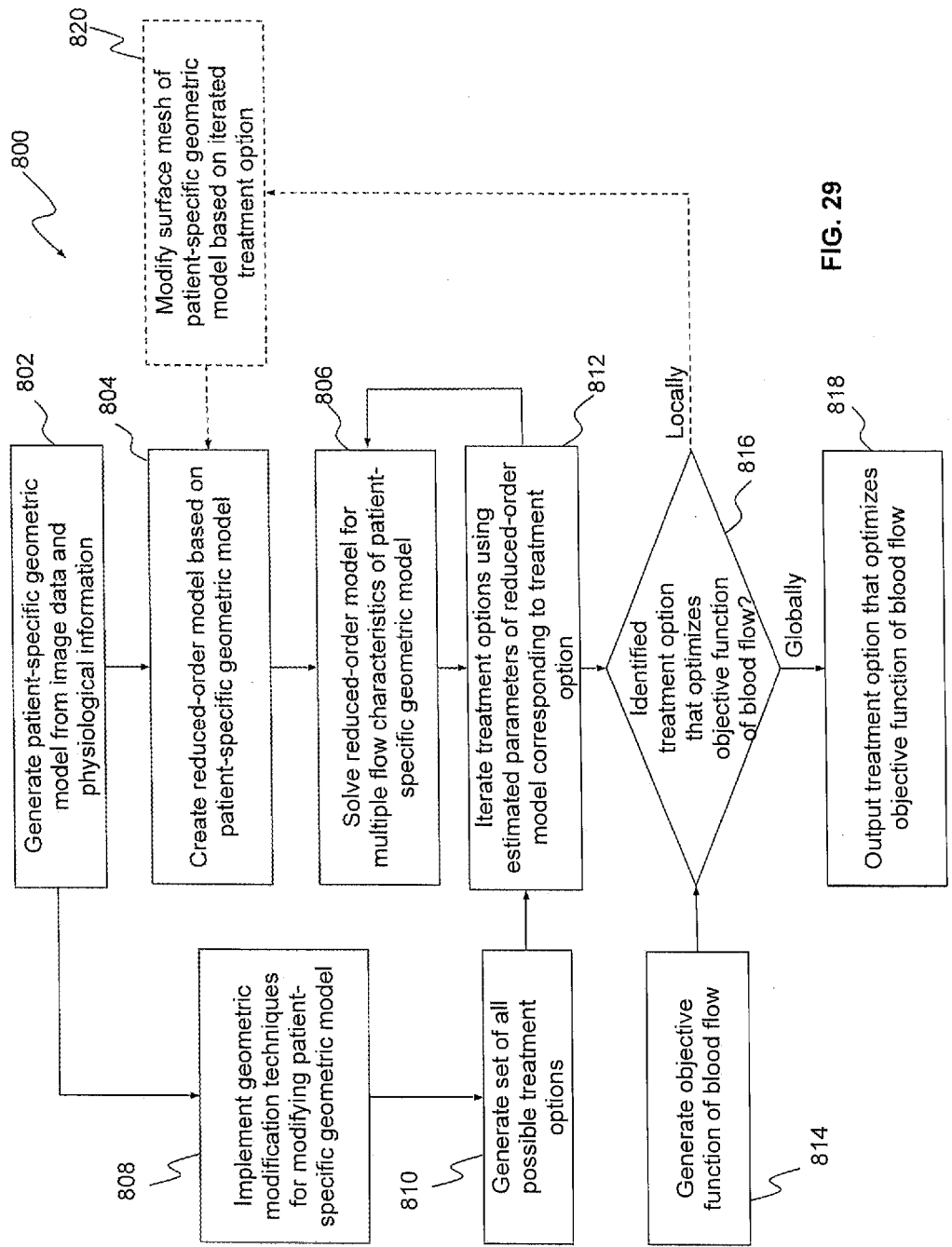
FIG. 29 is a flow chart of a method for determining an optimal treatment option by modifying a patient-specific geometric model.

FIG. 29 depicts a method 800 for automatically evaluating treatment options by modifying patient-specific geometric models. As depicted, method 800 may include generating a patient-specific geometric model from image data and physiological information (step 802). For example, the imaging data may include the CCTA data obtained in step 100 of FIG. 2, and the formed geometric model may be the solid model 320 of FIG. 8 generated in step 306 of FIG. 3, and/or the mesh 380 of FIGS. 17-19 generated in step 312 of FIG. 3.

Method 800 may then include segmenting the simulated blood flow model (e.g., as described above in connection with FIG. 14) based on the anatomical features of the model, and creating a reduced-order model based on the patient-specific geometric model (step 804). First, various techniques may be provided for segmenting the simulated blood flow model, including generating centerlines and sectioning based on the generated centerlines, or detecting branch points and sectioning based on the detected branch points. The diseased portions and stenoses may be identified, e.g., by measuring the cross-sectional area along the length of the centerline and calculating locally minimum cross-sectional areas. The segments may be replaced by components of a lumped parameter model, such as resistors, capacitors, inductors, etc., as described above in connection with FIG. 15. The individual values for the resistance, capacitance, inductance, and other variables associated with other electrical components used in the lumped parameter model may be derived from the simulated blood flow models. For example, for branches and portions between the branches and the portions with stenosis or diseased areas, information derived from the simulated blood flow model may be used to assign linear resistances to the corresponding segments.

A reduced order (e.g., zero-dimensional or one-dimensional) model may then be generated using the determined resistances. For example, the reduced order model may be a lumped parameter model generated as described above in connection with step 310 of FIG. 3. Thus, the lumped parameter model is a simplified model of the patient's anatomy that may be used to determine information about the coronary blood flow in the patient without having to solve the more complex system of equations associated with the mesh 380 of FIGS. 17-19.

The modified reduced order model may be solved to determine information about the coronary blood flow in the patient (step 806). For example, using the patient-specific three-dimensional geometric model, computational analysis may be performed, e.g., as described above in connection with step 402 of FIG. 3, to determine information about the patient's coronary blood flow. The computational analysis may output one or more three-dimensional patient-specific simulated blood flow models representing blood flow or other parameters, e.g., the simulated blood pressure model 50 of FIG. 1, the simulated blood flow model 52 of FIG. 1, the cFFR model 54 of FIG. 1, etc. Thus, multiple computational analyses may be used to obtain simulated blood flow models for various flow and pressure conditions to derive patient-specific, vessel-specific, and lesion-specific resistance functions for these complex geometries, as described above in connection with FIG. 15.

Meanwhile, method 800 may also involve implementing geometric modification techniques for modifying the generated patient-specific geometric model to reflect a plurality of treatment options (step 808). Any suitable computerized modeling or computerized-aided drafting technique may be used for modifying a mesh associated with a patient-specific geometric model. For example, in one embodiment, a geometric domain modification technique may be used to perform a constructive solid geometry (CSG) union for combining treated and original patient arterial geometry. In another embodiment, an elastic deformation modification technique may be used to deform a mesh model of original patient arterial geometry to the shape of proposed treated arterial geometry. Exemplary embodiments of geometric domain modification and elastic deformation modification techniques will be described in more detail below.

Method 800 may further include using one or more modification techniques to model all possible treatment options (step 810). For example, modification techniques may simulate the insertion of a stent in all possible locations of a patient's arterial trees. Modification techniques may simulate the insertion of all possible stents, including all combinations of radii and lengths of stents, and/or all commercially available stents, based on a database of known commercial stent geometries. Moreover, geometric modification techniques may simulate the insertion of a plurality of stents, in any suitable locations. For example, given a patient's arterial tree having a plurality of arterial branches, modification techniques may be used to identify every location along each arterial branch where a stent may be positioned. Moreover, the possible locations may be overlapping, such that a patient's geometric model is modified for a shift in stent location that is significantly shorter than the stent itself. Likewise, modification techniques may be applied for all possible locations of a bypass graft, and all possible sizes and orientations of bypass grafts. The computer system may also apply modification techniques for any possible combination of PCI and/or CABG interventions.

In one embodiment, the computing system may generate the set of possible treatment options for every single feasible location within a patient's coronary vasculature. In another embodiment, the computing system may generate the set of possible treatment options for sections of a patient's coronary vasculature having a predetermined threshold level of energy losses, or some other flow characteristic. For example, upon solving for a patient's coronary blood flow characteristics in step 806, a computing system may identify those segments having a predetermined blood flow characteristic, such as an FFR value below 0.75, or an FFR value that drops by more than 5% between arterial segments. The computing system may then generate a set of potential treatment options for those segments, using the geometric modification techniques described above, for all feasible types, sizes, and orientations of various stents and/or bypass grafts.

Given a set of all possible treatment options, method 800 may include performing an iterative solving of the reduced order model for all treatment options, using estimated parameters of the reduced order model that correspond to each treatment option (steps 812, 806). Specifically, the reduced order model may be efficiently executed for each possible treatment option. In one embodiment, the reduced order model may be a network of resistors that represent the intrinsic resistances of a three-dimensional computational fluid dynamic model. The intrinsic resistances may be calculated by selecting endpoints of resistive segments, determining pressures at those nodes, and flow through segments connecting these nodes, e.g., using pre-operative results solved for in step 806, and calculating resistances using Ohm's law. The reduced order model may be coupled to resistances defined as boundary conditions of the patient-specific geometry model.

In order to solve the reduced order model for each possible treatment option, estimated parameters associated with the possible treatment option may be used to modify the reduced order model. For example, in the case of a resistor model, a resistance value estimated for a stent may be inserted into the reduced order model at a suitable location for the stent. The resistance value estimated for the stent may be moved to any of a plurality of suitable locations for the stent, and the reduced order model may be solved for each possible location. As described above with respect to FIGS. 12-16, the reduced order model generated for each possible treatment option may be quickly solved using, for example, Ohm's law, Kirchhoff's current law, and/or Kirchhoff's voltage law.

In one embodiment, resistance values used in solving the reduced order model for each treatment option, may be estimated based on an analytical solution for fully-developed flow in a circular cylinder (i.e., as Poiseuille flow). For example, for a given stent or bypass, it may be assumed that fully-developed flow exists across the length and diameter of the known dimensions and geometry of the possible stent or bypass. The computer system may then analytically solve for a resistance value associated with such flow. As an alternative to such an analytical technique, resistance values associated with possible stent or bypass options may be obtained from historical data, such as a database or library of known resistance values associated with various known dimensions and geometries of previously implemented stents or bypass grafts. Thus, a reduced order model may be created and solved for each possible treatment option, using a resistance value calculated, estimated, or otherwise predicted to be associated with the type and location of the respective possible treatment option. Moreover, the reduced order model may be created and then solved with a simplified set of equations that allows for relatively rapid computation (e.g., compared to a full three-dimensional model) and may be used to solve for flow rate and pressure that may closely approximate the results of a full three-dimensional computational solution, given the respective treatment option. The reduced order model allows for relatively rapid iterations to model various different treatment options.

Method 800 may also include generating one or more objective functions of blood flow characteristics solved from the plurality of reduced order models (step 814). A suitable objective function may be a cost function, or any other multi-variable function that optimizes one or more variables, relative to one or more other variables. In one embodiment, a generated objective function may optimize one or more of the flow characteristics solved from the plurality of reduced order models corresponding to the plurality of treatment options. For example, the objective function may be designed to identify one or more treatment options that maximizes arterial flow, or minimizes FFR losses. In one embodiment, the objective function may be designed to identify one or more treatment options that optimize a Syntax score, as described in U.S. application Ser. No. 13/656,183 for Systems and Methods for Numerically Evaluating Vasculature, filed by Timothy A. Fonte et al. on Oct. 19, 2012, the entire contents of which is incorporated herein by reference. The objective function may be designed to maximize flow, minimize pressure changes, or optimize any other desired characteristic of blood flow. Thus, solving the objective function may enable identification of one or more of the treatment options (i.e., stent selection/location and/or bypass graft selection/location) that optimizes the desired characteristic. Because the objective function operates on results of the numerous reduced order models solved in steps 806, 812, the objective function may quickly and automatically evaluate the results of hundreds, thousands, or even tens of thousands of different treatment options.

In addition, the objective function may be configured to penalize certain undesirable characteristics of possible treatment options. Specifically, the objective function may be designed such that an optimum identified treatment is not necessarily the treatment with the absolute highest maximized or lowest minimized variable, e.g., because it may have one or more penalties. For example, the objective function may be designed to apply penalties to treatment options having more than one stent, and greater penalties with rising numbers of interventions (i.e., penalizing combinations of stents and bypass grafts). In one embodiment, the objective function may penalize one or more of: increasing numbers of stents and/or bypass grafts; decreasing of FFR values in larger vessels, smaller vessels; increasing proximity of (i.e., decreasing distance between) inserted stents; and the existence or number of bifurcations.

In one embodiment, the objective function may penalize certain treatment options based on actual and/or estimated monetary costs of the one or more treatment options. For example, the objective function may receive or access a library of known hospital fees, physician fees, medical device prices, insurance reimbursements, or any other monetary costs associated with different treatments. The costs may be known to vary based on various patient factors, geography of the procedure, the type of implanted medical device, the hospital or physician associated with the procedure, a complexity of a surgical procedure, and so on. Thus, for example, as complexity increases, or numbers of stents or bypasses increases, the projected or modeled costs of the treatment option may also increase, and the relevant treatment option may be penalized accordingly by the objective function.

In other words, the objective function may be designed to favor treatment options that are simple, e.g., using one stent or one bypass, and effective, e.g. resulting in significant outcomes for large vessels over smaller vessels, even if those treatment options do not result in the absolute most optimized blood flow characteristic. Such objective functions may result in the identification of one or more locally or globally optimized blood flow characteristics (step 816).

In one embodiment, when the objective function identifies a treatment option that optimizes a desired flow parameter (e.g., a global optimum that minimizes FFR, maximizes flow, etc.), method 800 may include outputting that treatment option (step 818), such as by displaying the identified treatment option. For example, method 800 may include displaying a patient-specific geometrical model as modified by the selected treatment option (e.g., stent or bypass graft). In addition, or alternatively, method 800 may include displaying a written or textual description of the selected treatment option. For example, method 800 may include displaying the type, location, and/or orientation of the stent and/or bypass graft that optimizes the objective function.

In one embodiment, when the objective function identifies a local optimum, such as an FFR value, pressure value, or flow value that is relatively optimal, but not necessarily the most optimal value, method 800 may optionally include modifying the surface mesh of the patient-specific model based on the iterated treatment option that results in a local optimum (step 820). Thus, a locally optimum treatment option may be used to refine or create a new reduced order model by modifying the patient-specific geometric model with the treatment option using one or more geometric modification techniques described with respect to step 808. Such a technique may facilitate efficient and automatic generation of revised surface meshes and reduced order models that are most likely to result in identifying an optimum treatment option. Of course, a treatment option identified by modifying a surface mesh based on iterated treatment option (step 820) and creating a corresponding reduced order model (step 804) may be output to a display, in relation to the patient-specific geometric model, three-dimensional flow model, and/or FFRct model (step 818).

Figure 30:
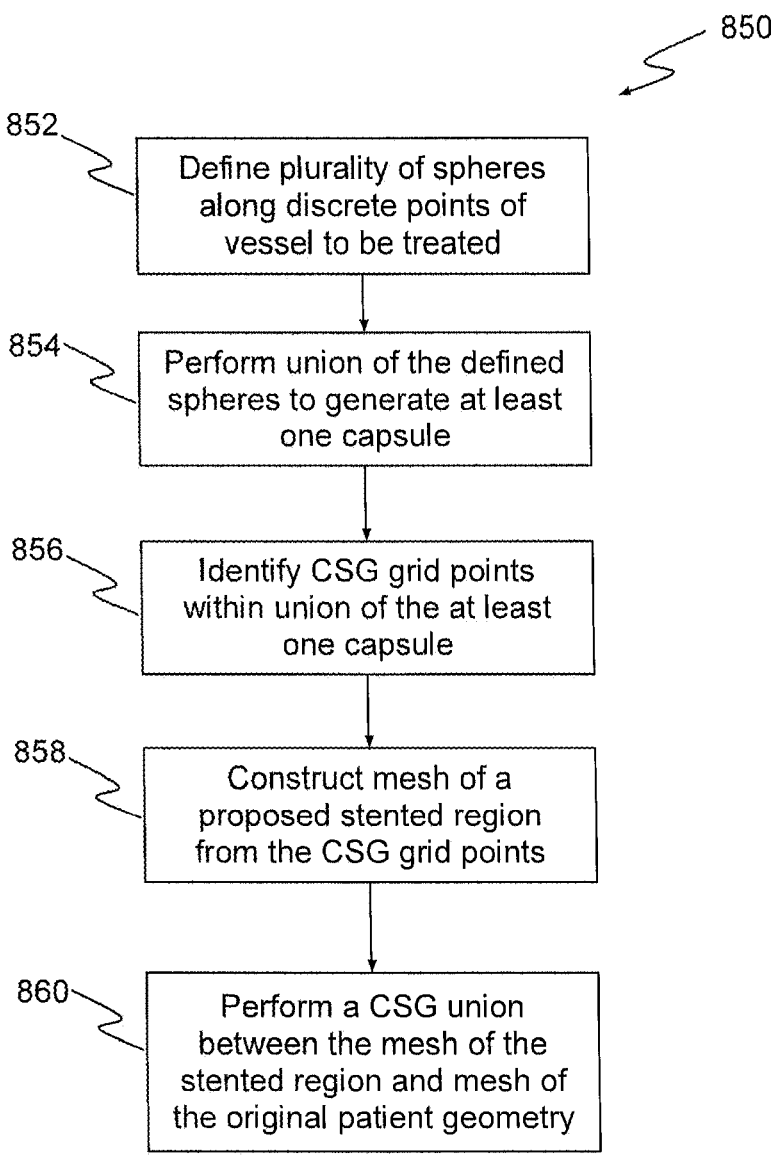
FIG. 30 depicts an exemplary embodiment of a method of a geometric domain modification technique for modifying a patient-specific geometric model.

As described above with respect to step 808, a plurality of different techniques may be implemented for modifying a patient-specific geometric model, both for generating a set of all possible treatment options, and for refining a surface mesh for generating a refined reduced order model of blood flow. FIG. 30 depicts a method 850 of a geometric domain modification technique for modifying a patient-specific geometric model. In general, geometric domain modification may involve augmenting a vessel diameter by performing a CSG union of a patient's original vessel geometry with a constructed geometry that represents a stented region.

In one embodiment, implicit functions may be used to construct the geometry of a stented region. As shown in FIG. 30, method 850 may include defining a plurality of spheres along discrete points of a vessel to be treated (step 852). For example, a sphere centered at the point $[c_x, c_y, c_z]$ with radius r may be described by the implicit function $(x-c_x)^2+(y-c_y)^2+(z-c_z)^2=r^2$. Thus, having defined a sequential number of discrete points along a vessel, every two consecutive points $(p_n, p_{n+1})$ along the path may be used to define a capsule.

Method 850 may then include performing a union of the defined spheres to generate at least one capsule (step 854). Specifically, as reflected in the diagram of FIG. 31A, each capsule may be defined as the union of the two spheres of specified radii at each point and the cone between them that linearly interpolates the two radii.

Figure 31B:
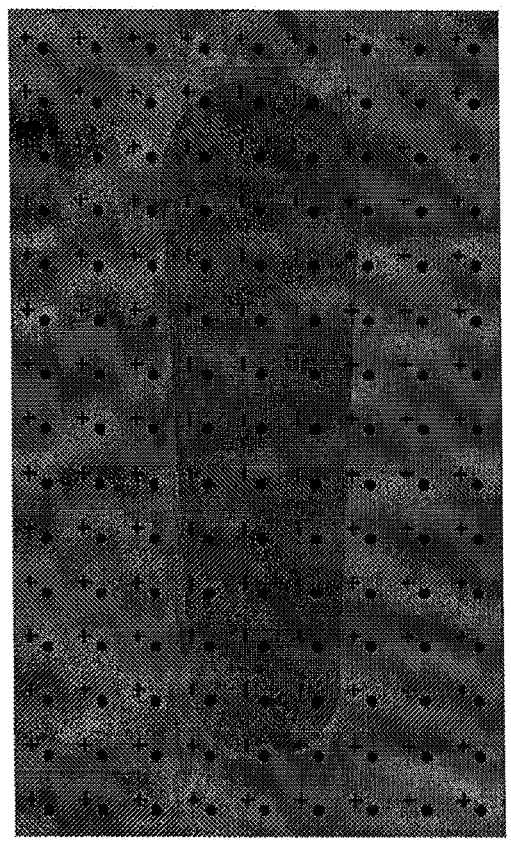
FIG. 31B depicts a diagram of another step of an exemplary method of a geometric domain modification technique for modifying a patient-specific geometric model.
Figure 31A:
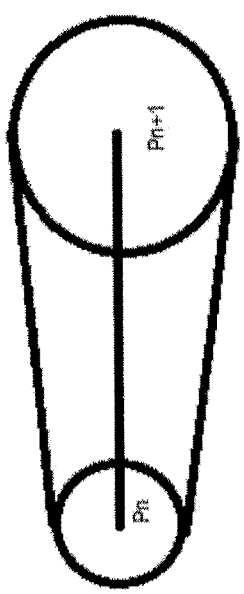
FIG. 31A depicts a diagram of a step of an exemplary method of a geometric domain modification technique for modifying a patient-specific geometric model.

Method 850 may then include identifying a plurality of CSG grid points within the union of the at least one capsule (step 856). Specifically, a computing system may construct a uniform CSG grid of adequate spacial resolution around the one or more capsules generated in step 854. FIG. 31B depicts one embodiment of a plurality of CSG grid points around a union forming a capsule. In one embodiment, for each grid point, a signed distance may be computed for each capsule, and the minimum value over all of the capsules may be stored at each grid point. In one embodiment, each signed distance may be the distance from a grid point to the closest point on a capsule, where, as shown in FIG. 31B, a positive sign may indicate the point lies outside the surface and a negative sign indicates the point lies inside the surface. Thus, step 856 may result in a grid of values that represent a union of all capsules generated in step 854.

Figure 32:
FIG. 32 depicts a graphical representation of a triangle mesh of an exemplary proposed stent geometry.

Method 850 may further include constructing a mesh of the proposed stented region from the CSG grid points generated in step 856 (step 858). For example, any suitable CSG technique, including Marching-Cubes or Dual-Contouring may be used to extract an explicit triangle mesh from the CSG grid, thereby representing a section of the vessel that contours to a proposed stent. FIG. 32 depicts a graphical representation of a triangle mesh of a proposed stent geometry, created by running a Marching-Cubes technique on a union of implicitly generated capsules.

Figure 33A:
FIG. 33A depicts a graphical representation of a triangle mesh of an exemplary original patient geometry having a stenosis portion that appears as a visible narrowing of a vessel.
Figure 33B:
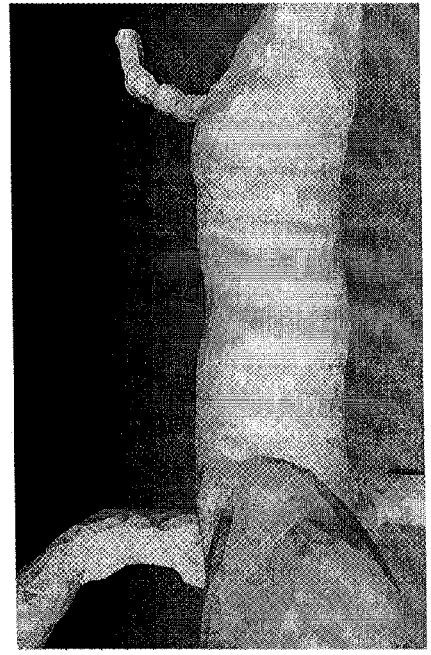
FIG. 33B depicts a graphical representation of a triangle mesh resulting from a union between the exemplary original patient geometry mesh depicted in FIG. 33A and the exemplary stent mesh geometry depicted in FIG. 32.

Method 850 may further include performing a CSG union between the mesh of the proposed stented region (as formed in step 858), and the mesh of the original patient geometry (step 860). FIG. 33A depicts a graphical representation of a triangle mesh of an original patient geometry having a stenosis portion that appears as a visible narrowing of a vessel. FIG. 33B depicts a graphical representation of a triangle mesh resulting from a CSG union between the original patient geometry mesh depicted in FIG. 33A and the stent mesh geometry depicted in FIG. 32. In other words, the geometrical mesh depicted in FIG. 33B reflects a merging or combining of the stent geometry generated in FIG. 32 and the stenosed geometry generated in FIG. 33A.

In addition to the geometric domain modification techniques described above with respect to FIGS. 30-33B, an elastic deformation modification technique may also or alternatively be used for modifying a patient-specific geometric model. FIG. 34 depicts an exemplary method 880 for performing an elastic deformation technique for modifying a patient-specific geometric model. In general, method 880 may involve deforming a surface mesh of a patient-specific geometric model around an explicit or implicit shape that represents a shape of a desired treatment option, such as a stent or bypass graft.

In one embodiment, method 880 may include obtaining a surface mesh of patient geometry to be deformed (step 882). For example, a surface mesh may be segmented for a section of an arterial vessel into which a stent may be inserted, and opened using finite element software, or any type of elastic deformation simulator. Method 880 may include setting material properties of the tissue to be deformed (step 884), and assigning those material properties to the surface mesh. For example, the material properties may define the realistic elasticity, etc. of actual vasculature tissue. Method 880 may then include applying known stent geometry to a desired collision geometry (step 886). For example, for any of the set of possible treatment options, including any suitable stent types, geometries, or sizes, method 880 may include inserting one or more geometric representations of such stents into the elastic deformation simulator as a collision geometry. Method 880 may then include executing the finite element or elastic deformation simulator to push the surface mesh of a patient's original tissue geometry to approach the surface of the inserted collision geometry (step 888). In one embodiment, the surface mesh geometry may be refined as desired to capture the effects of the collision while performing collision detection and response to avoid allowing surface geometry from self-intersecting.

While the present disclosure describes embodiments of geometric domain modification and elastic deformation modification, it will be appreciated that any suitable type of computerized graphics or other constructive solid geometry techniques may be used to modify models of patient geometry, for purposes of automatically identifying all possible sets of treatment options, and evaluating those identified treatment options.

As a result of the foregoing techniques, the accuracy of three-dimensional blood flow modeling may be combined with the computational simplicity and relative speed inherent in one-dimensional and lumped parameter modeling technologies. Three-dimensional computational methods may be used to numerically derive patient-specific one-dimensional or lumped parameter models that embed numerically-derived empirical models for pressure losses over normal segments, stenoses, junctions, and other anatomical features. Improved diagnosis for patients with cardiovascular disease may be provided, and planning of medical, interventional, and surgical treatments may be performed faster.

Also, the accuracy of three-dimensional computational fluid dynamics technologies may be combined with the computational simplicity and performance capabilities of lumped parameter and one-dimensional models of blood flow. A three-dimensional geometric and physiologic model may be decomposed automatically into a reduced-order one-dimensional or lumped parameter model. The three-dimensional model may be used to compute the linear or nonlinear hemodynamic effects of blood flow through normal segments, stenoses, and/or branches, and to set the parameters of empirical models. The one-dimensional or lumped parameter models may more efficiently and rapidly solve for blood flow and pressure in a patient-specific model, and display the results of the lumped parameter or one-dimensional solutions.

The reduced order patient-specific anatomic and physiologic model may be used to determine the effect of different medications or lifestyle changes (e.g., cessation of smoking, changes in diet, or increased physical activity) that alters heart rate, stroke volume, blood pressure, or coronary microcirculatory function on coronary artery blood flow. Such information may be used to optimize medical therapy or avert potentially dangerous consequences of medications. The reduced order model may also be used to determine the effect on coronary artery blood flow of alternate forms and/or varying levels of physical activity or risk of exposure to potential extrinsic force, e.g., when playing football, during space flight, when scuba diving, during airplane flights, etc. Such information may be used to identify the types and level of physical activity that may be safe and efficacious for a specific patient. The reduced order model may also be used to predict a potential benefit of percutaneous coronary interventions on coronary artery blood flow in order to select the optimal interventional strategy, and/or to predict a potential benefit of coronary artery bypass grafting on coronary artery blood flow in order to select the optimal surgical strategy.

The reduced order model may also be used to illustrate potential deleterious effects of an increase in the burden of arterial disease on coronary artery blood flow and to predict, using mechanistic or phenomenological disease progression models or empirical data, when advancing disease may result in a compromise of blood flow to the heart muscle. Such information may enable the determination of a "warranty period" in which a patient observed to be initially free from hemodynamically significant disease using noninvasive imaging may not be expected to require medical, interventional, or surgical therapy, or alternatively, the rate at which progression might occur if adverse factors are continued.

The reduced order model may also be used to illustrate potential beneficial effects on coronary artery blood flow resulting from a decrease in the burden of coronary artery disease and to predict, using mechanistic or phenomenological disease progression models or empirical data, when regression of disease may result in increased blood flow through the coronary arteries to the heart muscle. Such information may be used to guide medical management programs including, but not limited to, changes in diet, increased physical activity, prescription of statins or other medications, etc.

The reduced order model may also be incorporated into an angiography system to allow for live computation of treatment options while a physician examines a patient in a cardiac catheterization lab. The model may be registered to the same orientation as the angiography display, allowing side-by-side or overlapping results of a live angiographic view of the coronary arteries with simulated blood flow solutions. The physician may plan and alter treatment plans as observations are made during procedures, allowing for relatively rapid feedback before medical decisions are made. The physician may take pressure, FFR, or blood flow measurements invasively, and the measurements may be utilized to further refine the model before predictive simulations are performed.

The reduced order model may also be incorporated into a medical imaging system or workstation. If derived from a library of previous patient-specific simulation results, then the reduced order models may be used in conjunction with geometric segmentation algorithms to relatively rapidly solve for blood flow information after completing an imaging scan.

The reduced order model may also be used to model the effectiveness of new medical therapies or the cost/benefit of treatment options on large populations of patients. A database of multiple patient-specific lumped parameter models (e.g., hundreds, thousands, or more) may provide models to solve in relatively short amounts of time. Relatively quick iteration and optimization may be provided for drug, therapy, or clinical trial simulation or design. Adapting the models to represent treatments, patient responses to drugs, or surgical interventions may allow estimates of effectiveness to be obtained without the need to perform possibly costly and potentially risky large-scale clinical trials.

Any aspect set forth in any embodiment may be used with any other embodiment set forth herein. Every device and apparatus set forth herein may be used in any suitable medical procedure, may be advanced through any suitable body lumen and body cavity, and may be used for imaging any suitable body portion.

Various modifications and variations can be made in the disclosed systems and processes without departing from the scope of the disclosure. Other embodiments will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method for planning treatment for arterial stenotic lesions by processing patient-specific images of a patient, comprising:
    identifying a set of stenotic lesions in a patient's coronary arteries from medical image data of the patient;
    generating a plurality of treatment options for the set of stenotic lesions, wherein each of the plurality of treatment options corresponds to a stenting configuration in which one or more of the stenotic lesions are stented;
    calculating, for each of the plurality of treatment options, predicted hemodynamic metrics for the set of stenotic lesions resulting from the stenting configuration corresponding to that treatment option; and
    recommending a treatment option from the plurality of treatment options based on the predicted hemodynamic metrics for the set of stenotic lesions calculated for each of the plurality of treatment options, and based on a number of stents in the stenting configuration corresponding to each of the plurality of treatment options.

2. The method of claim 1, wherein recommending the treatment option from the plurality of treatment options further comprises:
    recommending the treatment option from the plurality of treatment options in order of maximal blood flow restoration based on the predicted hemodynamic metrics calculated for the set of stenotic lesions, with treatment options having stenting configurations with a smaller number of stents preferentially selected ahead of treatment options having stenting configurations with a larger number of stents if the predicted hemodynamic metrics calculated for the treatment options having the stenting configurations with the smaller number of stents indicate that a blood flow is sufficiently restored.

3. The method of claim 1, wherein recommending the treatment option from the plurality of treatment options further comprises:

recommending the treatment option from the plurality of treatment options based on the predicted hemodynamic metrics for the set of stenotic lesions calculated for each of the plurality of treatment options, by penalizing treatment options having stenting configurations in a stented anatomical region.

4. The method of claim 1, wherein calculating, for each of the plurality of treatment options, predicted hemodynamic metrics for the set of stenotic lesions resulting from the stenting configuration corresponding to that treatment option comprises:
calculating, for each of the plurality of treatment options, predicted fractional flow reserve (FFR) values for the set of stenotic lesions resulting from the stenting configuration corresponding to that treatment option.

5. The method of claim 4, wherein calculating, for each of the plurality of treatment options, predicted fractional flow reserve (FFR) values for the set of stenotic lesions resulting from the stenting configuration corresponding to that treatment option comprises:
adjusting a pressure drop simulated for the one or more of the stenotic lesions that are stented in the corresponding stenting configuration;
simulating blood flow and pressure in the coronary arteries of the patient with the adjusted pressure drop for the one or more of the stenotic lesions that are stented; and
calculating FFR values for each of the set of stenotic lesions based on the simulated blood flow and pressure in the coronary arteries of the patient.

6. The method of claim 5, wherein adjusting a pressure drop simulated for the one or more of the stenotic lesions that are stented in the corresponding stenting configuration comprises:
adjusting the pressure drop simulated for the one or more of the stenotic lesions that are stented in the corresponding stenting configuration to a pressure drop of zero.

7. The method of claim 5, wherein adjusting a pressure drop simulated for the one or more of the stenotic lesions that are stented in the corresponding stenting configuration comprises:
adjusting the pressure drop simulated for the one or more of the stenotic lesions that are stented in the corresponding stenting configuration to a predetermined value representing partial opening of the one or more stenotic lesions that are stented.

8. The method of claim 1, wherein the plurality of treatment options comprises a respective treatment option corresponding to each possible stenting configuration of one or more of the set of stenotic lesions.

9. The method of claim 1, further comprising:
displaying, for each of the plurality of treatment options, a respective figure showing results of calculating the predicted hemodynamic metrics for the set of stenotic lesions resulting from the stenting configuration corresponding to that treatment option.

10. The method of claim 2, further comprising:
displaying a plurality of results of calculating the predicted hemodynamic metrics for the set of stenotic lesions resulting from the stenting configuration corresponding to each of the plurality of treatment options.

11. The method of claim 2, further comprising:
displaying a model of the patient's coronary arteries; and
in response to a user selecting one of a plurality of treatment options, displaying the stenting configuration corresponding to the selected treatment option and the hemodynamic metrics calculated for the set of stenotic lesions resulting from the stenting configuration corresponding to the selected treatment option.

12. The method of claim 2, further comprising:
displaying a model of the patient's coronary arteries; and
in response to a user selection of one or more stent locations on the model of the patient's coronary arteries, displaying the hemodynamic metrics calculated for the set of stenotic lesions for a treatment option corresponding to the stenting configuration indicated by the user selection of the one or more stent locations.

13. The method of claim 2, wherein identifying a set of stenotic lesions in a patient's coronary arteries from medical image data of the patient comprises:
extracting a patient-specific anatomical model of the coronary arteries from the medical image data;
detecting a plurality of stenotic lesions in the coronary arteries using the patient-specific anatomical model of the coronary arteries;
estimating a hemodynamic metric for each of the plurality of stenotic lesions; and
identifying a set of hemodynamically relevant stenotic lesions from the plurality of stenotic lesions based on the hemodynamic metric estimated for each of the plurality of stenotic lesions.

14. The method of claim 13, wherein estimating a hemodynamic metric for each of the plurality of stenotic lesions comprises:
simulating blood flow and pressure in the coronary arteries using a computational model of coronary circulation; and
estimating the hemodynamic metric for each of the plurality of stenotic lesions based on a simulated pressure change across each of the plurality of stenotic lesions.

15. The method of claim 13, wherein estimating a hemodynamic metric for each of the plurality of stenotic lesions comprises: estimating a fractional flow reserve (FFR) value for each of the plurality of stenotic lesions.

16. A system for planning treatment for arterial stenotic lesions by processing patient-specific images of a patient, the system comprising:
at least one computer system configured for:
identifying a set of stenotic lesions in a patient's coronary arteries from medical image data of the patient;
generating a plurality of treatment options for the set of stenotic lesions, wherein each of the plurality of treatment options corresponds to a stenting configuration in which one or more of the stenotic lesions are stented;
calculating, for each of the plurality of treatment options, predicted hemodynamic metrics for the set of stenotic lesions resulting from the stenting configuration corresponding to that treatment option; and
recommending a treatment option from the plurality of treatment options based on the predicted hemodynamic metrics for the set of stenotic lesions calculated for each of the plurality of treatment options, and based on a number of stents in the stenting configuration corresponding to each of the plurality of treatment options.

17. The system of claim 16, wherein calculating, for each of the plurality of treatment options, predicted hemodynamic metrics for the set of stenotic lesions resulting from the stenting configuration corresponding to that treatment option comprises:
calculating, for each of the plurality of treatment options, predicted fractional flow reserve (FFR) values for the set of stenotic lesions resulting from the stenting configuration corresponding to that treatment option.

18. The system of claim 17, wherein calculating, for each of the plurality of treatment options, predicted fractional flow reserve (FFR) values for the set of stenotic lesions resulting from the stenting configuration corresponding to that treatment option comprises:
adjusting a pressure drop simulated for the one or more of the stenotic lesions that are stented in the corresponding stenting configuration;
simulating blood flow and pressure in the coronary arteries of the patient with the adjusted pressure drop for the one or more of the stenotic lesions that are stented; and
calculating FFR values for each of the set of stenotic lesions based on the simulated blood flow and pressure in the coronary arteries of the patient.

19. The system of claim 16, wherein the plurality of treatment options comprises a respective treatment option corresponding to each possible stenting configuration of one or more of the set of stenotic lesions.

20. A non-transitory computer readable medium storing computer program instructions for planning treatment for arterial stenotic lesions by processing patient-specific images of a patient, the computer program instructions when executed by a processor causes the processor to perform operations comprising:
identifying a set of stenotic lesions in a patient's coronary arteries from medical image data of the patient;
generating a plurality of treatment options for the set of stenotic lesions, wherein each of the plurality of treatment options corresponds to a stenting configuration in which one or more of the stenotic lesions are stented;
calculating, for each of the plurality of treatment options, predicted hemodynamic metrics for the set of stenotic lesions resulting from the stenting configuration corresponding to that treatment option; and
recommending a treatment option from the plurality of treatment options based on the predicted hemodynamic metrics for the set of stenotic lesions calculated for each of the plurality of treatment options, and based on a number of stents in the stenting configuration corresponding to each of the plurality of treatment options.

* * * * *